United States Patent
Sapiro et al.

(10) Patent No.: US 12,048,574 B2
(45) Date of Patent: Jul. 30, 2024

(54) METHOD FOR A BRAIN REGION LOCATION AND SHAPE PREDICTION

(71) Applicant: Owl Navigation, Inc., Edina, MN (US)

(72) Inventors: Guillermo Sapiro, Durham, NC (US); Noam Harel, Minnetonka, MN (US); Yuval Duchin, Minnetonka, MN (US); Jin Young Kim, Durham, MN (US)

(73) Assignee: Owl Navigation, Inc., Edina, MN (US)

( * ) Notice: Subject to any disclaimer, the term of this patent is extended or adjusted under 35 U.S.C. 154(b) by 0 days.

(21) Appl. No.: 18/140,437

(22) Filed: Apr. 27, 2023

(65) Prior Publication Data

US 2023/0293130 A1 Sep. 21, 2023

Related U.S. Application Data

(63) Continuation of application No. 17/137,022, filed on Dec. 29, 2020, now Pat. No. 11,771,389, which is a
(Continued)

(51) Int. Cl.
*A61B 6/50* (2024.01)
*A61B 5/00* (2006.01)
(Continued)

(52) U.S. Cl.
CPC .............. *A61B 6/501* (2013.01); *A61B 5/055* (2013.01); *A61B 6/5217* (2013.01);
(Continued)

(58) Field of Classification Search
CPC ....... A61B 6/501; A61B 5/055; A61B 6/5217; A61B 6/5294; A61B 5/0035; A61B 6/032;
(Continued)

(56) References Cited

U.S. PATENT DOCUMENTS 7,646,898 B1 1/2010 Nowinski et al.
7,911,208 B2 3/2011 Reisman
(Continued)

FOREIGN PATENT DOCUMENTS

JP 2008-508043 A 3/2008
JP 2010-510825 A 4/2010
(Continued)

OTHER PUBLICATIONS

Abosch, Aviva et al., An Assessment of Current Brain Targets for Deep Brain Stimulation Surgery with Susceptibility-Weighted Imaging at 7 Tesla, Congress of Neurological Surgeons, Dec. 2010, vol. 67, No. 6, pp. 1745-1756.
(Continued)

*Primary Examiner* — Molly Wilburn

(57) ABSTRACT

A volumetric segmentation method is disclosed for brain region analysis, in particular but not limited to, regions of the basal ganglia such as the subthalamic nucleus (STN). This serves for visualization and localization within the sub-cortical region of the basal ganglia, as an example of prediction of a region of interest for deep brain stimulation procedures. A statistical shape model is applied for variation modes of the STN, or the corresponding regions of interest, and its predictors on high-quality training sets obtained from high-field, e.g., 7T, MR imaging. The partial least squares regression (PLSR) method is applied to induce the spatial relationship between the region to be predicted, e.g., STN, and its predictors. The prediction accuracy for validating the invention is evaluated by measuring the shape similarity and the errors in position, size, and orientation between manually segmented STN and its predicted one.

16 Claims, 14 Drawing Sheets

Related U.S. Application Data continuation of application No. 15/457,355, filed on Mar. 13, 2017, now Pat. No. 10,885,149, which is a continuation of application No. 14/317,925, filed on Jun. 27, 2014, now Pat. No. 9,600,778.

(60) Provisional application No. 61/929,053, filed on Jan. 18, 2014, provisional application No. 61/841,955, filed on Jul. 2, 2013.

(51) Int. Cl.
| | |
|---|---|
| A61B 5/055 | (2006.01) |
| A61B 6/00 | (2024.01) |
| A61B 6/03 | (2006.01) |
| A61B 6/12 | (2006.01) |
| A61B 6/46 | (2024.01) |
| A61B 34/10 | (2016.01) |
| G06F 16/50 | (2019.01) |
| G06F 18/25 | (2023.01) |
| G06N 5/04 | (2023.01) |
| G06N 20/00 | (2019.01) |
| G06T 7/00 | (2017.01) |
| G06T 7/11 | (2017.01) |
| G06T 7/33 | (2017.01) |
| G16H 30/20 | (2018.01) |
| G16H 50/20 | (2018.01) |

(52) U.S. Cl.
CPC .......... *A61B 6/5294* (2013.01); *G06F 16/50* (2019.01); *G06F 18/251* (2023.01); *G06N 5/04* (2013.01); *G06N 20/00* (2019.01); *G06T 7/0012* (2013.01); *G06T 7/11* (2017.01); *G06T 7/337* (2017.01); *G16H 30/20* (2018.01); *G16H 50/20* (2018.01); *A61B 5/0035* (2013.01); *A61B 6/032* (2013.01); *A61B 6/037* (2013.01); *A61B 6/12* (2013.01); *A61B 6/469* (2013.01); *A61B 6/5247* (2013.01); *A61B 6/563* (2013.01); *A61B 2034/107* (2016.02); *A61B 2576/026* (2013.01); *G06T 2207/10081* (2013.01); *G06T 2207/10088* (2013.01); *G06T 2207/20128* (2013.01); *G06T 2207/30016* (2013.01)

(58) Field of Classification Search
CPC .......... A61B 6/037; A61B 6/12; A61B 6/469; A61B 6/5247; A61B 6/563; A61B 2034/107; A61B 2576/026; G06F 16/50; G06F 18/00; G06F 18/251; G06N 5/04; G06N 20/00; G06T 7/0012; G06T 7/11; G06T 7/337; G06T 2207/10081; G06T 2207/10088; G06T 2207/20128; G06T 2207/30016; G16H 30/20; G16H 50/20
See application file for complete search history.

(56) References Cited

U.S. PATENT DOCUMENTS

| | | | |
|---|---|---|---|
| 7,925,328 | B2 | 4/2011 | Urquhart et al. |
| 8,160,676 | B2 | 4/2012 | Gielen et al. |
| 8,160,677 | B2 | 4/2012 | Gielen et al. |
| 8,175,677 | B2 | 5/2012 | Sayler et al. |
| 8,189,885 | B2 | 5/2012 | Saha et al. |
| 8,209,027 | B2 | 6/2012 | Butson et al. |
| 8,355,553 | B2 | 1/2013 | Fidrich et al. |
| 8,369,931 | B2 | 2/2013 | Paek et al. |
| 9,412,076 | B2 | 8/2016 | Sapiro et al. |
| 9,600,778 | B2 * | 3/2017 | Sapiro ............... A61B 5/055 |
| 10,885,149 | B2 * | 1/2021 | Sapiro ............... A61B 6/5217 |
| 11,263,749 | B1 * | 3/2022 | Purushottam ......... G16H 15/00 |
| 2003/0097219 | A1 | 5/2003 | O'Donnell et al. |
| 2003/0228042 | A1 | 12/2003 | Sinha |
| 2005/0070781 | A1 | 3/2005 | Dawant et al. |
| 2005/0171558 | A1 | 8/2005 | Abovitz et al. |
| 2005/0245810 | A1 | 11/2005 | Khamene et al. |
| 2006/0017749 | A1 | 1/2006 | McIntyre et al. |
| 2006/0045347 | A1 | 3/2006 | Xiao et al. |
| 2007/0127790 | A1 | 6/2007 | Lau et al. |
| 2008/0097193 | A1 | 4/2008 | Karmarkar |
| 2008/0103547 | A1 | 5/2008 | Okun et al. |
| 2008/0123922 | A1 | 5/2008 | Gielen et al. |
| 2008/0123923 | A1 | 5/2008 | Gielen et al. |
| 2008/0312525 | A1 | 12/2008 | Park et al. |
| 2009/0034812 | A1 | 2/2009 | Nowinski et al. |
| 2009/0118635 | A1 | 5/2009 | Lujan et al. |
| 2009/0134873 | A1 | 5/2009 | Cho et al. |
| 2009/0220136 | A1 | 9/2009 | Bova et al. |
| 2009/0226060 | A1 | 9/2009 | Gering et al. |
| 2009/0287271 | A1 | 11/2009 | Blum et al. |
| 2010/0019767 | A1 | 1/2010 | Cho et al. |
| 2010/0061632 | A1 | 3/2010 | Young et al. |
| 2010/0067761 | A1 * | 3/2010 | Jakobsson ............... G06T 7/149 382/131 |
| 2010/0074499 | A1 | 3/2010 | Wels et al. |
| 2011/0040351 | A1 | 2/2011 | Butson et al. |
| 2012/0027272 | A1 * | 2/2012 | Akinyemi ............... G06T 7/11 382/128 |
| 2012/0098838 | A1 | 4/2012 | Lehmann et al. |
| 2012/0165652 | A1 | 6/2012 | Dempsey |
| 2012/0314919 | A1 | 12/2012 | Sparks et al. |
| 2013/0030499 | A1 | 1/2013 | Pouratian |
| 2013/0039550 | A1 | 2/2013 | Blum et al. |
| 2013/0104066 | A1 | 4/2013 | Soederstroem |
| 2013/0116749 | A1 | 5/2013 | Carlton et al. |
| 2013/0172727 | A1 * | 7/2013 | Mori ............... G06T 7/0012 600/407 |
| 2014/0364721 | A1 | 12/2014 | Lee et al. |
| 2015/0010223 | A1 | 1/2015 | Sapiro et al. |
| 2015/0012466 | A1 | 1/2015 | Sapiro et al. |
| 2015/0025548 | A1 | 1/2015 | Franklin et al. |
| 2015/0157858 | A1 | 6/2015 | Mcintyre et al. |
| 2015/0246231 | A1 | 9/2015 | Martens et al. |
| 2016/0300352 | A1 * | 10/2016 | Raj ............... G06V 10/764 |
| 2017/0193161 | A1 | 7/2017 | Sapiro et al. |
| 2019/0117072 | A1 * | 4/2019 | Pereira ............... G16H 50/70 |
| 2021/0118549 | A1 | 4/2021 | Sapiro et al. |
| 2022/0395244 | A1 * | 12/2022 | Taubmann ............... G06T 7/30 |

FOREIGN PATENT DOCUMENTS

| | | |
|---|---|---|
| JP | 2011-512999 A | 4/2011 |
| WO | 2007/058632 A1 | 5/2007 |
| WO | 2009/002072 A3 | 3/2009 |
| WO | 2015/002846 A2 | 1/2015 |

OTHER PUBLICATIONS

Alterman, Ron L. et al. "Preparation for Surgey", Chapter 5 fom Movement Disorder Surgery: The Essentals, by Roy A.E. Bakay, .Copyrgt. 2009, 18 pages.

Ashkan, K. et al., Variability of the Subthalamic Nucleus: The Case for Direct MRI Guided Targeting, British Journal of Neurosurgery, 2007, vol. 21(2), pp. 197-200.

Benabid, Alim Louis et al., "Implantation of Muitipie Electrodes and Robotic Techniques", Chapter 9 from Movement Disorder Surgery: The Essentials, by Roy A.E. Bakay, .Copyrgt. 2009, 20 pages.

Brierey, J.B., Beck, Elisabeth, The Signifcance in Human Stereotactic Brain Surgery of indivdual Variation in the Diencephalon and Globus Pallidus, Journal of Neurology Neurosurgery, Psychiatry, vol. 22. 1959, pp. 287-298.

Cho, Zang Hee et al., "New Brain Atlas-Mapping the Human Brain in Vivo with 7.0 T MRI and Comparison with Postmortem Histology: Will These Images Change Modern Medicine?", Apr. 2008, Wiley Periodicals, Inc. (C) 2008, 7 pages.

(56) References Cited

OTHER PUBLICATIONS

Cootes T. et al., "The Use of Active Shape Models For Locating Structures in Medical Images", Image and Vision Computing, vol. 12, No. 6, Jul. 1994.
Davies, Keith G. & Daniluk, Slawomir, C. (2008), Stereotactic Targeting of the Subthalamic Nucleus: Relevance of Magnetic Resonance-Based Evaluation of Interindividual Variation in Diencephalic Anatomy, Stereotactic and Functional Neurosurgery, 86, 330-331. Doi:10.1159/000160156, www.karger.com/sfn.
Duchin, Yuval et al., Feasibility of Using Ultra-High Field (7T) MRI for Clinical Surgical Targeting, May 2012, vol. 7, Issue 5, e37328, PLos One, www.plosone.com, pp. 1-10.
Eller, Jorge L. et al., "Deep Brain Stimulation for Tremor", Chapter 11 from Movement Disorder Surgery: The Essentials, by Roy A.E. Bakay, .Copyrgt. 2009, 19 pages.
Ericsson et al., "Construction of a patient-specific atlas of the brain: Application to normal aging", Biomedical Imaging: From Nano To Macro, 2008, ISBI 2008, 5th IEEE International Symposium on, Piscataway, NJ USA, May 14, 2008, pp. 480-483.
Extended European Search Report issued in EP Application No. 19169514.7, issued May 29, 2019, 10 pages.
Extended European Search Report issued in EP14820217.9, mailed Jul. 10, 2017, 11 pages.
Gross, Robert E. et al., "Anesthesia for Movement Disorder Surgery" Chapter 6 from Movement Disorder Surgery: The Essentials, by Roy A.E. Bakay, .Copyrgt. 2009, 19 pages.
Hariz. Marwan I. et al., "Stereotactic Surgery without Microelectrode Recording", Chapter 8 from Movement Disorder Surgery: The Essentials, by Roy A.E. Bakay, .Copyrgt. 2009, 17 pages.
Henderson, Jaimie M., "Frameless Functional Stereotactic Approaches", Chapter 10 from Movement Disorder Surgery: The Essentials, by Roy A.E. Bakay, .Copyrgt. 2009, 19 pages.
International Preliminary Report on Patentability received for PCT Patent Application No. PCT/US2014/044675, mailed on Jan. 14, 2016, 21 pages.
International Search Report and Written Opinion received for PCT Patent Application No. PCT/US2014/044675, mailed on Jan. 8, 2015, 23 pages.
Invitation to Pay Additional Fees received for PCT Patent Application No. PCT/US2014/044675, mailed on Oct. 24, 2014, 2 pages.
Kim J. et al., "Clinical Deep Brain Stimulation Region Prediction Using Regression Forests From High-Field Mri", IEEE ICIP, 2015. (Date precludes use).
Kim J. et al., "Clinical Subthalamic Nucleus Prediction From High-Field Brain MRI", IEEE, 2015. (Date precludes use).
Kim J. et al., "Robust Prediction of Clinical Deep Brain Stimulation Target Structures via the Estimation of Influential High-Field MR Atlases", MICCAI 2015, Part II, LNCS 9350, pp. 587-594, 2015. (Date precludes use).
Kopell, Brian Harris et al., "Setting up a Movement Disorder Surgery Practice", Chapter 3 from Movement Disorder Surgery: The Essentials, by Roy A.E. Bakay, .Copyrgt. 2009, 29 pages.
Lad, Shivanand P. et al., "The Future of Treatment for Advanced Parkinson Disease", Chapter 17 from Movement Disorder Surgery: The Essentials, by Roy A.E, Bakay, .Copyrgt. 2009, 17 pages.
Larson, Paul S. et al., Magnetic Resonance Imaging of Implanted Deep Brain Stimulators; Experience in a Large Series, Stereotactic and Functional Neurosurgery 2008; 86:92-100, DOI: 10.1159/000112430, www.karger.com/fnc, Pub. Online Dec. 17, 20007.
Larson, Paul, C. (2011), An Optimized System for Interventional Magnetic Resonance Imaging-Guided Stereotactic Surgery: Preliminary Evaluation of Targeting Accuracy, Stereotactic Surgery: Preliminary Evaluation of Targeting Accuracy, vol. 70, 95-103, DOI 10.1227/NEU.0b013e31822f4a91, www.neurosurgery-online.com.
Lenget, Christophe et al., Comprehensve in vivo Mapping of the Basal Ganglia and Thalamus Connectome in Individual Subject using High Resolution 7T MRI, Abstract, Neuroscience 2011, 2 pages.
Lenglet, Christophe et al., Comprehensive in vivo Mapping of the Human Basal Ganglia and thalamic Connectome in Individuals Using 7T MRI, Jan. 2012, vol. 7, Issue 1,E29153, PLos One. www.plosone.com, pp. 1-14.
Lenglet, Christophe et al., Visualization of the Human Basal Ganglia and Thalamic Ciruits in Individual Using 7T MRI, Proc. Intl. Soc. Mag. Reson. Med. 20, (2012), p. 425.
McIntyre, Cameron C. et al., "Rational for Movement Disorder Surgery", Chapter 2 from Movement Disorder Surgery: The Essentials, by Roy A.E. Bakay, .Copyrgt. 2009, 19 pages.
McIntyre, Cameron et al. U.S. Appl. No. 61/913,349, filed Dec. 8, 2013, 66 pages.
McIntyre, Cameron et al. U.S. Appl. No. 61/954,638, filed Mar. 18, 2014, 26 pages.
Montgomery, Erin B. Jr., "Deep Brain Stimulation Programming", Chapter 13 from Movement Disorder Surgery: The Essentials, by Roy A.E. Bakay, .Copyrgt. 2009, 33 pages.
Partial Supplementary European Search Report issued in EP Application No. 14820217, mailed Mar. 15, 2017, 7 pages.
Patel, Nikunj K., Khan, Sadaquate & Gill, Steven S., C. (2008), Comparison of Atlas-and Magnetic-Resonance-Imaging-Stereotactic Targeting of the Subthalamic Nucleus in the Surgical Treatment of Parkinson's Disease, Stereotactic and Functional Neurosurgery 86, 153-161., DOI: 10.1159/000120427, www.karger.com/fnc.
Rao et al., "Hierarchical statistical shape analysis and prediction of sub-cortical brain structures", Medical Image Analysis, vol. 12, No. 1, Feb. 1, 2008, pp. 55-68.
Rijkers Kim M.D., et al, The Microanatomical Envioment of the Subthalamic Nucleus, Journal of Neuosugery, vol. 107, 2007, pp. 198-201.
Sapiro, Guillermo et al. U.S. Appl. No. 61/841,955, filed Jul. 2, 2013, 33 pages.
Sapiro, Guillermo et al. U.S. Appl. No. 61/929,053, filed Jan. 18, 2014, 71 pages.
Shah, Rahul S., et al., Deep Brain Stimulation: Technology at the Cutting Edge, Journal of Clinical Neurology, 2010, vol. 6, pp. 167-182.
Sierens, Diane et al., "Stereotactic Surgery with Microelectrode Recordings", Chapter 7 from Movement Disorder Surgery: The Essentials, by Roy A.E, Bakay, .COPYRGT. 2009, 44 pages.
Starr, Philip, M.D. et al., Implantation of Deep Brain Stimulators into the Subthalamic Nucleus: Technical Approach and Magnetic Resonance Imaging-Verified Lead Locations, Journal of Neurosurgery, vol. 97, 2002, pp. 370-387.
Starr, Phillip A., "Avoiding Complications and Correcting Errors", Chapter 14 from Movement Disorder Surgery: The Essentials, by Roy A.E. Bakay, .Copyrgt. 2009, 19 pages.
Van der Kolk, Anja G et al., Clinical Applications of 7 T MRI in the Brain, European Jounal of Radiology, 2013, vol. 82, pp. 708-718.

* cited by examiner

METHOD FOR A BRAIN REGION LOCATION AND SHAPE PREDICTION

REFERENCE TO RELATED APPLICATIONS

This application is a continuation of U.S. patent application Ser. No. 17/137,022, filed Dec. 29, 2020, entitled Method for a Brian Region Location and Shape Prediction, which is a continuation of U.S. patent application Ser. No. 15/457,355, filed Mar. 13, 2017, entitled Method for a Brian Region Location and Shape Prediction, now U.S. Pat. No. 10,885,149, issued Jan. 5, 2021, which is a continuation of U.S. patent application Ser. No. 14/317,925, filed Jun. 27, 2014, entitled Method for a Brian Region Location and Shape Prediction, now U.S. Pat. No. 9,600,778, issued Mar. 21, 2017, which claims the benefit of U.S. Provisional Application Nos. 61/841,955, filed Jul. 2, 2013, entitled Methods and Systems for a High-Resolution Brain Image Pipeline and Database Program, and 61/929,053, filed Jan. 18, 2014, entitled Method for a Brain Region Location and Shape Prediction, each of which is herein incorporated by reference in its entirety and for all purposes.

TECHNICAL FIELD

Embodiments disclosed herein relate generally to medical imaging systems and in particular to the generation and use of patient-specific multimodal brain high-quality atlases to support medical procedure, included but not limited to brain surgery and including deep brain stimulation (DBS).

BACKGROUND

The use of medical images to guide neurosurgical procedures is ubiquitous. The brain is a complex organ, full of structures and vessels that are at once crucial to a patient's survival and well-being, and difficult to perceive unaided by imaging technology. Three-dimensional imaging techniques, and particularly the magnetic resonance imaging techniques using various contrast weights, that have become available, have made the various internal features of the brain easier to discern, paving the way for subtler, safer, and more effective procedures. However, even the current battery of imaging technology, and in particular that available in common clinical settings, is not sufficient to portray the needed information for the physician to assure the best outcomes.

The subthalamic nucleus (STN) is a small oval (lens-shaped) nucleus in the brain, located ventral to the thalamus. In terms of anatomy, it is the major part of subthalamus and is part of the basal ganglia system. Often, issues such as sensitivity limitations of the current clinical imaging methods available to physicians make it difficult to obtain images showing target areas such as the STN used as a deep brain stimulation target for treating Parkinson's disease. The STN is often used here as an example of the invention, while the invention applies to other brain structures as well, some critical for DBS and some for other brain procedures.

To enhance patient images, models known as atlases created using archived images or diagrams are matched and fitted to the patient images. However, these atlases are often themselves limited and are not patient-specific and/or adapted to the particular patient, and generally do not offer a sufficient range of image types and brains imaged to guarantee a useful match to the patient's brain and particular procedure. Atlases derived from post-mortem sampling, while possibly high resolution, are typically derived from single individual, and thereby do not reflect an accurate representation of the anatomy of the brain of the patient currently being evaluated. Atlases derived from averages of multiple brains do not portray the anatomical features of a specific patient and are therefore less accurate.

The STN within the sub-cortical region of the Basal ganglia is a crucial targeting structure for Deep brain stimulation (DBS) surgery, in particular for alleviating Parkinson's disease (PD) symptoms. Volumetric segmentation of such small and complex structure, which is elusive in clinical MRI protocols, is thereby a pre-requisite process for reliable DBS targeting of PD. While direct visualization and localization of the STN is facilitated with advanced high-field 7 T MR Imaging, such high fields are not always clinically available. The STN is an example of a target of interest that needs to be well-localized and not readily available in clinical settings.

As mentioned, Deep brain stimulation (DBS) is a widely used neurosurgical intervention for the treatment of neuro-degenerative diseases such as Parkinson's disease (PD), Essential tremor, and psychiatric disorders. In particular, it has been reported that the DBS of the STN structure has important clinical efficacy for advanced PD. Accurate positioning of the electrodes into the STN is critical for a successful DBS procedure, since slight misplacement even within STN region may result in severe side effects.

Various targeting approaches have been reported for the STN localization in the DBS procedure. Some of those methods refer to anatomical information such as the inter-commissural distances and the ventricles, based on atlases, to localize the STN. However, in such indirect generic atlas-based targeting procedures, the variability in the position and size of the STN across individual subjects needs to be further analyzed in the context of large populations to evaluate the applicability of the STN currently used atlases.

Recent studies have addressed this issue by assessing the variability in the position and size of the STN based on the midcommissural point across PD patients. More reliable targeting approaches are based on the direct visualization and localization of the STN on the individual subject's MRI.

Recent advances in high magnetic field, for example 7 Tesla (T), MR imaging techniques allow to directly identify small and complex anatomical structures, thanks to the superior contrast and high resolution. Furthermore, subject specific 3D structures and their connectivity within the Basal ganglia and thalamic have been modeled, exploiting the benefits of 7 T MRI, especially with the combination of multi-contrast MR images such as susceptibility-weighted image (SWI) and T2-weighted (T2W) image. Unfortunately, such high quality visualization is not always possible with standard clinical 1.5 T (or 3 T) MRI protocols. In addition to the localization, the accurate segmentation that provides spatial information such as location, dimension, and orientation of the DBS target structures in three dimensions is also a pre-requisite for the optimal electrode placement. This is in part due to the potential of lower therapeutically benefits or side-effects resulting from inadequate positioning of the DBS electrode in the STN (for PD) or other areas of other diseases.

Manual segmentation is both time consuming and mainly driven by anatomical subjectivity due in part to the lack of clear visualization with clinical, often low-field, MRI protocols. The automatic (or semi-automatic) segmentation of the STN structure is still challenging since it is small, complex shape with relatively unclear boundaries with its adjacent structure, although as mentioned above, superior contrast and high resolution at 7 T MRI enable us to directly visualize and identify its location and shape. Other brain structures have similar characteristics of being difficult to localize in clinical settings and can be facilitated by high quality atlases.

Of numerous automated segmentation techniques, statistical shape model-based segmentations such as active shape models have shown their effectiveness in various applications of medical imaging. These approaches statistically model the variability of target structures across subjects and search for the best-fit by minimizing criteria that combine the shape model and the subject-specific information. The accuracy of these segmentations depends on the initialization and the quality of the actual input (i.e., subject) data. Moreover, morphological variations of brain structures across the population have been analyzed using statistical shape models.

Recent studies have proposed regression-based shape prediction approaches using statistical shape models, considering correlations between different shapes of structures. Sub-cortical brain structures are predicted by combining canonical correlation analysis and partial least squares regression (PLSR). Several regression models for the shape prediction are compared, considering the uncertainty on landmark points, and incorporating relevant predictors to further improve femur and tibia predictions based on their sparse observation, instead of the regression approach, has built a joint input-output distribution model based on the statistical shape model with various uncertainties for the shape prediction. Furthermore, estimation of confidence regions for the predicted target shape has been investigated. These shape prediction methods enable to estimate the target structures even on data with limited information within regions of interest.

SUMMARY

The current disclosure extends the above-mentioned works in order to predict the position and shape of the STN, here used as example, explicitly exploiting the spatial relationship with its neighboring structures. Sub-cortical structures that have anatomical proximity with the STN and are possible to segment using standard targeting processes on 7 T MRI or even conventional 1.5 T/3 T MR imaging, are considered as predictors of the STN. We model the variation on shapes and poses of the STN and its predictors across training sets obtained from 7 T MR data using a statistical shape model. The spatial dependency between the STNs and its predictors is then extracted by the PLSR method, while other methods exploiting such relationships could be employed as well. Given the shape and pose of pre-segmented predictors for the STN on the real 7T or 1.5 T MR data from the specific subject, we estimate the complete shape and pose of the STN on that subject using the learned spatial dependency. Again, this is mostly illustrated here for the STN but this approach is general for other areas of interest.

A method for high-resolution automatic estimation and prediction of the shape, position, size, and orientation of components of the basal ganglia, such as the STN, and other brain structures is disclosed. The method is based on receiving a training set of preferably high-resolution and high-field magnetic resonance (single and multi-contrast) images, a set of individual patient data (clinical magnetic resonance) and possibly also CT images for prediction analysis.

The method also includes combining the information from the training set and the patient's set to predict components in the patient's set, obtaining basal ganglia structures, or other regions of interest, variation modes and its predictors from the training set. Moreover, the method includes applying a statistical shape model to brain region of interest (e.g. basal ganglia structures), variation modes and subthalamic nucleus predictors and applying a partial least squares regression method or other statistical analysis tools to the variation modes and its predictors.

In addition, the method includes extracting a relationship between the shape and location of subthalamic nucleus and the shape and location of the predictors; exploiting such relationship to predict the relevant shape (e.g., subthalamic nucleus, STN), and its location for the patient's data; incorporating the predicted shape and location into the patient's clinical images and transferring back, via an electronic medium, the patient's data with the incorporated prediction into the clinical setting.

The variation of the method include cases when the predictors belong to basal ganglia, the being Substantia Nigra, Red Nucleus, internal Globus Pallidus and Thalamus; or their combination.

The method according to claim 1, wherein the electronic device includes at least one of 7 Tesla, 3 Tesla or 1.5 Tesla magnet both for the dataset and the patient's data.

In a related set of invention, the at least one additional brain image comprises an image of the brain of the same patient. Alternatively, at least one image in the set of brain images comprises a T1-weighted magnetic resonance image. According to some embodiments, at least one image in the set of brain images comprises a T2-weighted magnetic resonance image. According to some additional embodiments, at least one image in the set of brain images comprises a susceptibility-weighted magnetic resonance image. In another embodiment, at least one image in the set of brain images comprises a diffusion-weighted magnetic resonance image. In some embodiments, at least one image in the set of brain images comprises a functional magnetic resonance image. At least one image in the set of brain images comprises a computed tomography image, in another embodiment. Under an additional embodiment, at least one image in the set of brain images comprises a positron emission tomography image. In another embodiment, at least one image in the set of brain images comprises a magnetic resonance image taken with field strength of 3 Tesla or higher. According to another embodiment, at least one image in the set of brain images comprises an angiographic image of the arteries in the depicted brain. At least one image in the set of brain images comprises a venographic image of the veins in the depicted brain according to another embodiment.

Another embodiment involves maintaining, by the electronic device, a database of brain images, and retrieving the at least one additional brain image from that database. In a related embodiment, the database contains images belonging to at least two image types, including multiple modalities and contrasts, and retrieving the brain image from the database further comprises determining which of the at least two image types will produce the best patient-specific atlas for the intended clinical purpose, and retrieving an image belonging to that image type from the database. In another embodiment, the database contains images belonging to at least two image types, and retrieving the brain image from the database further comprises determining which of the at least two image types will produce the best patient-specific atlas for a particular portion of the patient brain, and retrieving an image belonging to that image type from the database. In another embodiment, retrieving the brain image from the database further comprises maintaining patient information concerning the patient brain image, maintaining patient information concerning each image maintained in the database, and retrieving an image from the database having patient information matching the patient information concerning the patient brain image. In still another embodiment, retrieving the brain image from the database further comprises locating an image in the database that matches the patient image and retrieving the matching image. Under another embodiment, retrieving the brain image from the database further comprises locating more than one image in the database that matches the patient image and retrieving the matching images. Under another embodiment, retrieving the brain image from the database further comprises receiving, by the at least one electronic device, an instruction specifying a particular image in the database and retrieving the specified image.

Alternatively, displaying the patient-specific atlas further comprises identifying a region of interest in the patient-specific atlas, and emphasizing that region of interest in the displayed atlas. Another embodiment involves identifying at least two regions of interest, and combining images of the at least two regions of interest to create the patient-specific atlas. Under another embodiment, the patient-specific atlas is used to guide a surgical procedure. Another embodiment involves using the image to guide an implantation procedure. An additional embodiment involves receiving at least one post-implantation image showing the brain of the patient after the insertion of an implant, merging the post-implantation image with the composite image to form a post-implantation patient-specific composite image, and displaying the post-implantation composite image. Still another embodiment involves using the patient-specific atlas to guide a procedure involving non-invasive energy exchange with the patient's brain.

Typically, the system for a high-resolution brain image pipeline, the system comprising an electronic device, a brain image retrieval component, executing on the electronic device, and receiving a set of brain images comprising an image of a patient's brain and at least one additional brain image, an atlas generation component, executing on the electronic device, and merging the patient brain image with the at least one additional brain image to produce a patient-specific atlas, and a display component, executing on the electronic device and displaying the composite image.

Other aspects, embodiments and features of the system and method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the system and method shown where illustration is not necessary to allow those of ordinary skill in the art to understand the system and method.

A method is disclosed for a high-resolution brain image pipeline, the method comprising receiving, by an electronic device, a set of brain images comprising an image of a patient's brain and at least one additional brain image, merging, by the electronic device, the patient brain image with the at least one additional brain image to produce a patient-specific atlas, and displaying, by the electronic device, the patient-specific atlas.

In a related set of embodiments, the at least one additional brain image comprises an image of the brain of the same patient. In other embodiments, at least one image in the set of brain images comprises a T1-weighted magnetic resonance image. According to some embodiments, at least one image in the set of brain images comprises a T2-weighted magnetic resonance image. According to some additional embodiments, at least one image in the set of brain images comprises a susceptibility-weighted magnetic resonance image. In another embodiment, at least one image in the set of brain images comprises a diffusion-weighted magnetic resonance image. In some embodiments, at least one image in the set of brain images comprises a functional magnetic resonance image. At least one image in the set of brain images comprises a computed tomography image, in another embodiment. Under an additional embodiment, at least one image in the set of brain images comprises a positron emission tomography image. In another embodiment, at least one image in the set of brain images comprises a magnetic resonance image taken with field strength of 3 Tesla or higher. According to another embodiment, at least one image in the set of brain images comprises an angiographic image of the arteries in the depicted brain. At least one image in the set of brain images comprises a venographic image of the veins in the depicted brain according to another embodiment.

Another embodiment involves maintaining, by the electronic device, a database of brain images, and retrieving the at least one additional brain image from that database. In a related embodiment, the database contains images belonging to at least two image types, including multiple modalities and contrasts, and retrieving the brain image from the database further comprises determining which of the at least two image types will produce the best patient-specific atlas for the intended clinical purpose, and retrieving an image belonging to that image type from the database. In another embodiment, the database contains images belonging to at least two image types, and retrieving the brain image from the database further comprises determining which of the at least two image types will produce the best patient-specific atlas for a particular portion of the patient brain, and retrieving an image belonging to that image type from the database. In another embodiment, retrieving the brain image from the database further comprises maintaining patient information concerning the patient brain image, maintaining patient information concerning each image maintained in the database, and retrieving an image from the database having patient information matching the patient information concerning the patient brain image. In still another embodiment, retrieving the brain image from the database further comprises locating an image in the database that matches the patient image and retrieving the matching image. Under another embodiment, retrieving the brain image from the database further comprises locating more than one image in the database that matches the patient image and retrieving the matching images. Under another embodiment, retrieving the brain image from the database further comprises receiving, by the at least one electronic device, an instruction specifying a particular image in the database and retrieving the specified image.

According to an additional embodiment, displaying the patient-specific atlas further comprises identifying a region of interest in the patient-specific atlas, and emphasizing that region of interest in the displayed atlas. Another embodiment involves identifying at least two regions of interest, and combining images of the at least two regions of interest to create the patient-specific atlas. Under another embodiment, the patient-specific atlas is used to guide a surgical procedure. Another embodiment involves using the image to guide an implantation procedure. An additional embodiment involves receiving at least one post-implantation image showing the brain of the patient after the insertion of an implant, merging the post-implantation image with the composite image to form a post-implantation patient-specific composite image, and displaying the post-implantation composite image. Still another embodiment involves using the patient-specific atlas to guide a procedure involving non-invasive energy exchange with the patient's brain.

Also claimed is a system for a high-resolution brain image pipeline, the system comprising an electronic device, a brain image retrieval component, executing on the electronic device, and receiving a set of brain images comprising an image of a patient's brain and at least one additional brain image, an atlas generation component, executing on the electronic device, and merging the patient brain image with the at least one additional brain image to produce a patient-specific atlas, and a display component, executing on the electronic device and displaying the composite image.

Other aspects, embodiments and features of the system and method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the system and method shown where illustration is not necessary to allow those of ordinary skill in the art to understand the system and method.

BRIEF DESCRIPTION OF THE DRAWINGS

The preceding summary, as well as the following detailed description of the disclosed system and method, will be better understood when read in conjunction with the attached drawings. For the purpose of illustrating the system and method, presently preferred embodiments are shown in the drawings. It should be understood, however, that neither the system nor the method is limited to the precise arrangements and instrumentalities shown.

DETAILED DESCRIPTION

Figure 1:
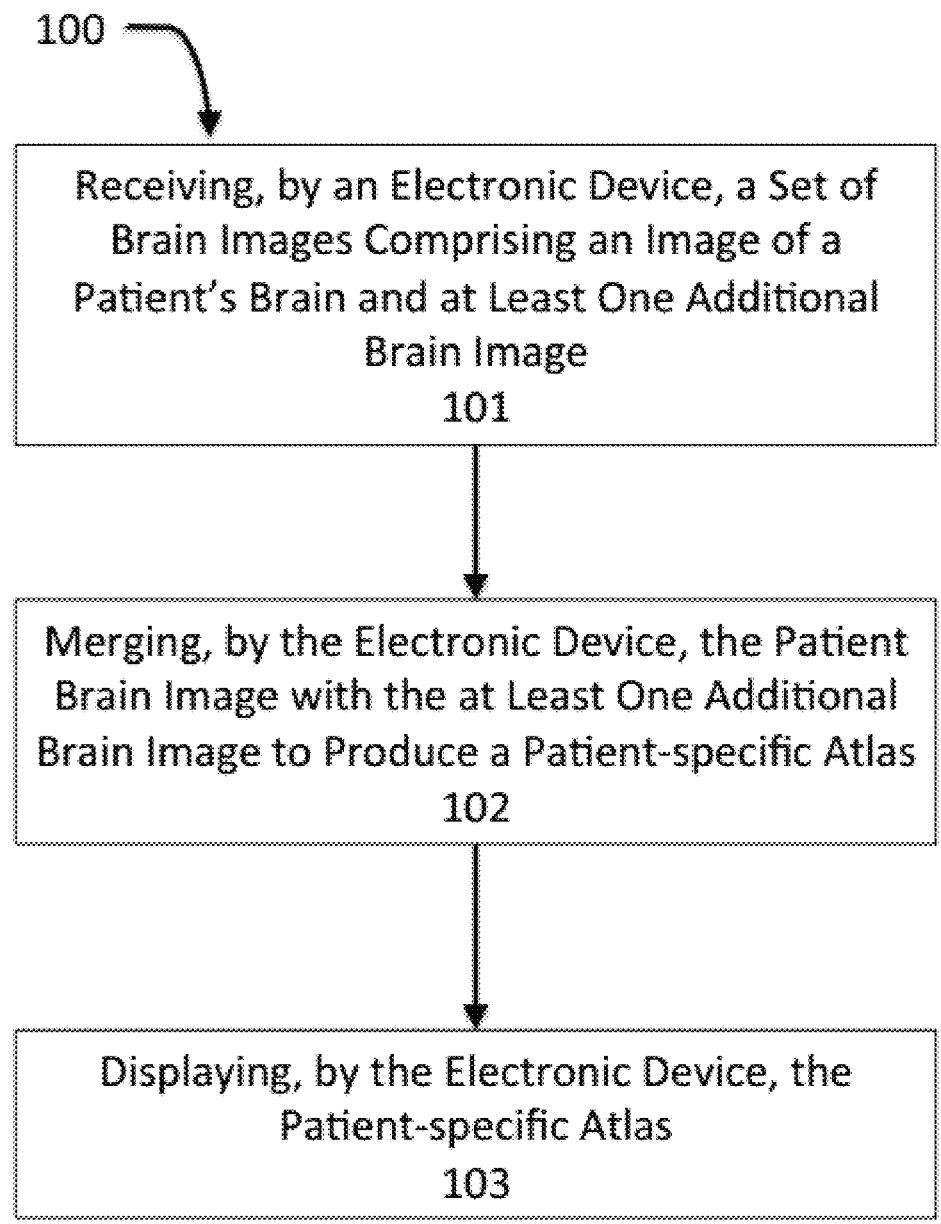
FIG. 1 is a flow chart illustrating the high-resolution brain image pipeline method.

Recent advantages in high field MRI technologies enable direct visualization and localization, in-vivo, of sub-cortical structures such as STN and GPi, critical for DBS targeting for motor diseases such as PD. Visualization of these regions in three dimensions will provide the surgical DBS targeting and post-surgery programming more reliable and effective. However, it remains a challenging problem to automatically delineate, for example, the STN region since it is very small and complex with unclear separation between adjacent structures such as the SN. In particular, it is not possible to segment the STN in such direct ways when using images acquired under standard low-field clinical protocols, or when the data has limited field of view within the region.

A method is disclosed for a (high-resolution) automatic shape prediction of the STN or other brain structures of relevance for the brain procedure; STN here and in the whole document used as a descriptive example. The method exploits the spatial dependency of the STN on its adjacent structures as predictors, some of which are easy to localize with standard clinical procedures.

First, a statistical shape model has been disclosed for variation modes of the STN and its predictors on a set of high-quality training sets obtained from high-field, e.g., 7T, MR imaging or other high-field data.

Second, the partial least squares regression (PLSR) method is disclosed to induce the spatial relationship between the STN and its predictors. Other methods can be used for inducing such relationship, and the STN is here used as example of an important area for brain surgery, deep brain stimulation in particular.

Prediction accuracy at training time can be evaluated by measuring the shape similarity and the errors in position, size, and orientation between manually segmented structure (e.g., STN) and its predicted one. This can be used to define predictors for a given structure of interest.

Definitions. As used in this description and the accompanying claims, the following terms shall have the meanings indicated, unless the context otherwise requires.

An "electronic device" is defined as including personal computers, laptops, tablets, smart phones, and any other electronic device capable of supporting an application as described herein.

A device or component is "coupled" to an electronic device if it is so related to that device that the product or means and the device may be operated together as one machine. In particular, a piece of electronic equipment is coupled to an electronic device if it is incorporated in the electronic device (e.g. a built-in camera on a smart phone), attached to the device by wires capable of propagating signals between the equipment and the device (e.g. a mouse connected to a personal computer by means of a wire plugged into one of the computer's ports), tethered to the device by wireless technology that replaces the ability of wires to propagate signals (e.g. a wireless BLUETOOTH® headset for a mobile phone), or related to the electronic device by shared membership in some network consisting of wireless and wired connections between multiple machines (e.g. a printer in an office that prints documents to computers belonging to that office, no matter where they are, so long as they and the printer can connect to the internet).

"Data entry devices" is a general term for all equipment coupled to an electronic device that may be used to enter data into that device. This definition includes, without limitation, keyboards, computer mice, touch-screens, digital cameras, digital video cameras, wireless antennas, Global Positioning System devices, audio input and output devices, gyroscopic orientation sensors, proximity sensors, compasses, scanners, specialized reading devices such as fingerprint or retinal scanners, and any hardware device capable of sensing electromagnetic radiation, electromagnetic fields, gravitational force, electromagnetic force, temperature, vibration, or pressure.

An electronic device's "manual data entry devices" is the set of all data entry devices coupled to the electronic device that permit the user to enter data into the electronic device using manual manipulation. Manual entry devices include without limitation keyboards, keypads, touch-screens, trackpads, computer mice, buttons, and other similar components.

An electronic device's "display" is a device coupled to the electronic device, by means of which the electronic device can display images and results from the analysis. Display includes without limitation monitors, screens, television devices, printed material, and projectors. To "maintain" data in the memory of an electronic device means to store that data in that memory in a form convenient for retrieval as required by the algorithm at issue, and to retrieve, update, or delete the data as needed.

The disclosed method addresses the prediction problem, and in a particular example for the STN, by exploiting learned spatial information between the STN and its predictors—substantia nigra (SN), red nucleus (RN), internal globus pallidus (GPi), and Thalamus (Tha)—using highly detailed information obtained from the high-field (for example 7T) MR training data. Neighboring structures that are highly correlated with the STN and can be easily delineated on individual subject data (from the 7T or even clinical 1.5 T magnet) are exploited as predictors, and then the spatial dependency between them is used to predict the full shape of the STN. Accordingly, SN, RN, GPi, and Tha structures, which are adjacent to the STN and fully visible on the 7 T MR imaging, are utilized as predictors to predict the STN on the 7T MR data. However, on the 1.5 T MR (clinical) imaging, since it is difficult to identify SN, GPi, and Tha, the RN that is still visible is chosen as a predictor of the STN.

In the proposed disclosure, the STN prediction problem is addressed using a statistical shape model and, the PLSR method as an example. Surface point coordinate vectors, in correspondence, across the training sets, represent the STN and its predictors. The generalized Procrustes analysis for surface point coordinates of the STN and its predictor gives pose parameters, locally aligning each structure across the training set. A kernel principal components analysis is then performed on the aligned surface point coordinates for the STN and its predictor across the training set, representing each shape parameter in lower dimensional space.

The PLSR then determines the relationships between shape parameters and poses of the STN and its predictors across the training set. Given the shape parameters and poses of the predictors of the STN on the real dataset (7 T or even 1.5 T MRI), those of the STN are predicted using their learned relationship. Finally, the complete shape of the STN is estimated, mapping the predicted shape parameters onto the original space and transforming them with the predicted poses. The STN is here used as in the rest of the document as a demonstrating example.

FIG. 1 illustrates the high-resolution brain image pipeline technique 100 which can be used in combination with the disclosure. Thus, the method 100 includes receiving, by an electronic device, a set of brain images comprising an image of a patient's brain and at least one additional brain image (possible of the same subject, in one embodiment; and from a database in another embodiment) (101). In addition, the method 100 includes merging, by the electronic device, the patient brain image with the at least one additional brain image to produce a patient-specific atlas (102). The method 100 also includes displaying, by the electronic device, the patient-specific atlas (103).

The method 100 includes receiving, by an electronic device, a set of brain images comprising an image of a patient's brain and at least one additional brain image (101). The brain image retrieval component 402 performs this step in some embodiments. In some embodiments, the at least one additional brain image comprises an image of the brain of the same patient. According to some embodiments, at least one image in the set of brain images comprises a T1-weighted magnetic resonance image. In some embodiments the T1-weighted MR image has a resolution of 1×1×1 mm$^3$ or better, where better indicates a higher resolution or improved signal to noise ratio. In some embodiments, at least one image in the set of brain images comprises a T2-weighted magnetic resonance image. The T2-weighted image in some embodiments has a resolution of 0.4×0.4×1 mm$^3$ or better. In some embodiments, at least one image in the set of brain images comprises a susceptibility-weighted (SWI) magnetic resonance image. The SWI in some embodiments has a resolution of 0.4×0.4×0.8 mm$^3$ or better. In some embodiments, at least one image in the set of brain images comprises a diffusion-weighted magnetic resonance image (DWI). The DWI image in some embodiments has a resolution of 1.5×1.5×1.5 mm$^3$ or better. The DWI images may also be enhanced using tractography to show neural pathways of interest. In some embodiments, such tractography is done in the whole dataset. In some embodiments, tractography is done between regions of interest. In some embodiments, tractography is done from the location of the DBS electrode to the whole brain or particular regions of interest. In some embodiments, the DWI images are taken with a high number of diffusion gradient trajectories, creating more accurate tractography. In some embodiments, the DWI images are taken with 55 distinct gradient trajectories. In some embodiments, the DWI images are taken with more than 55 distinct gradient trajectories. In some embodiments, at least one image in the set of brain images comprises a functional magnetic resonance image (fMRI). The fMRI according to some embodiments has a resolution of 1.5× 1.5×1.5 mm$^3$ or better. In some embodiments the above-described resolutions are achieved through the use of higher-strength magnetic fields in acquiring the MR image. In some embodiments at least one image in the set of brain images comprises a magnetic resonance image taken with field strength of 3 Tesla or higher. In some embodiments, the magnetic field is approximately 7 Tesla, occupying a range between 6.5 and 7.5 Tesla. In some embodiments, the magnetic field is stronger than 7 Tesla; for instance, the magnetic field may be 11.7 Tesla. The magnetic field may be stronger than 11.7 Tesla.

Figure 2:
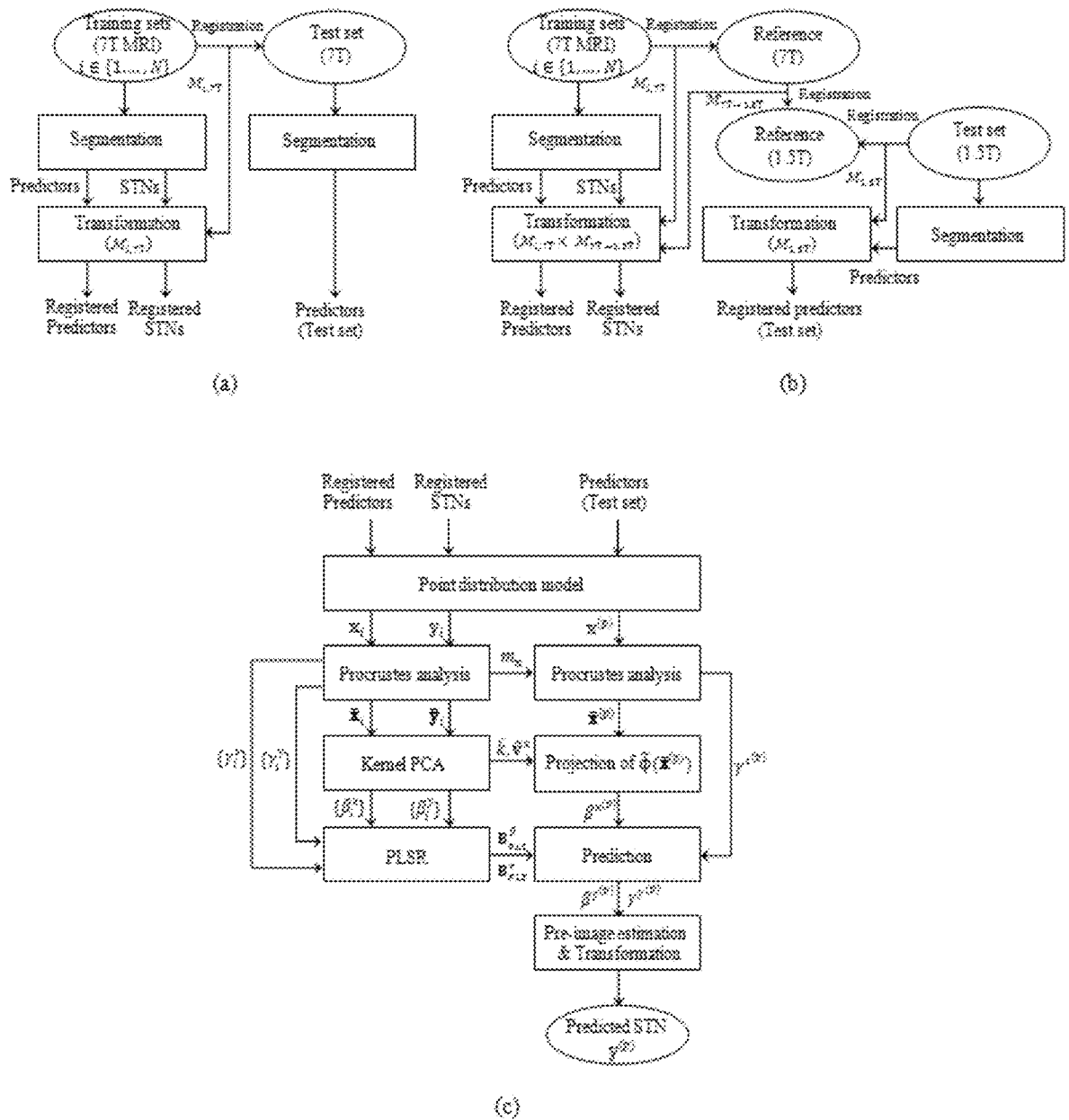
FIG. 2 is a schematic overview for the STN (or other brain structures) prediction. (a) Registration process for prediction on the high-field (e.g., 7 T) test data. (b) Registration process for prediction on the clinical (e.g., 1.5 T) test data. Note that reference data on 7 T and 1.5 T was scanned from the same subject. (c) Prediction framework.

An overview of the (STN here used as demonstrative example) prediction framework is presented in FIG. 2. The disclosure proposes the MRI Data Acquisition using training datasets of MRI that obtained using the high-field (7T) MRI (Magnex Scientific, UK). For each dataset, T2W images and SWI were utilized to obtain manual segmentations for the STN and its neighboring structures as predictors within the Basal ganglia and thalamus region across the training set (that includes STN, SN, RN and all the relevant structures). In addition, another set of subjects were also scanned at both 1.5 T or clinical MRI (T1W and T2W images) and (for validation as well) 7 T MRI. The 7 T MRI, coronal T2W images and SWI, were also utilized (for validation) to manually segment the STN and its neighboring structures. The 7 T MR images were then registered onto the T1W 1.5 T or clinical MR data of the same subject for the STN prediction and its validation.

The acquisition protocol for each 7 T MRI includes: i) T2W image acquisition with a 2D turbo spin echo sequence using the following parameters: field of view (FOV)=205× 205×36 mm3 with 0.4×0.4×2.0 mm3 resolution, repetition time/echo time (TR/TE)=5000/57 msec, flip angle=120°, bandwidth=220 Hz/pixel, with an acceleration factor of 2 (generalized auto-calibrating partially parallel acquisition (GRAPPA)) along the phase-encoding direction. The total acquisition time was approximately 7 min for one average. This protocol was repeated twice, to obtain both axial and coronal images of the midbrain. ii) SWI acquisition with a 3D flow-compensated gradient echo sequence using the following parameters: FOV=180×180×60 mm3 with 0.4× 0.4×1.0 mm3 resolution, TR/TE=28/20 msec, flip angle=15°, bandwidth=120 Hz/pixel, with an acceleration factor of 2 (GRAPPA) along the phase-encoding direction. One average was used, for a total acquisition time of approximately 7 min. This protocol was also repeated twice, to obtain both axial and coronal images of the midbrain.

Other protocols can be used as well combined with the other embodiments of this disclosure.

The 1.5 T MRI is acquired with the following standard clinical protocols: i) T1W image was acquired using commercial Siemens T1W AX T1 MPR clinical protocol with the following image parameters: FOV=192×256×176 mm3 with 0.98×0.98×1 mm resolution, TR=1650 ms; TE=3.02 ms, nominal flip angle of 15°, bandwidth of 179 Hz/pixel. ii) T2W image was acquired using a commercial Siemens T2W AX T2 3D SPC (Spin Echo) clinical protocol with the following image parameters: FOV: 172×230×192 mm3 with 0.72×0.72×2.0 mm3 resolution, TR/TE 2500/249 msec, Flip Angle 120 deg, bandwidth of 539 Hz/pixel and 2 averages.

Figure 3:
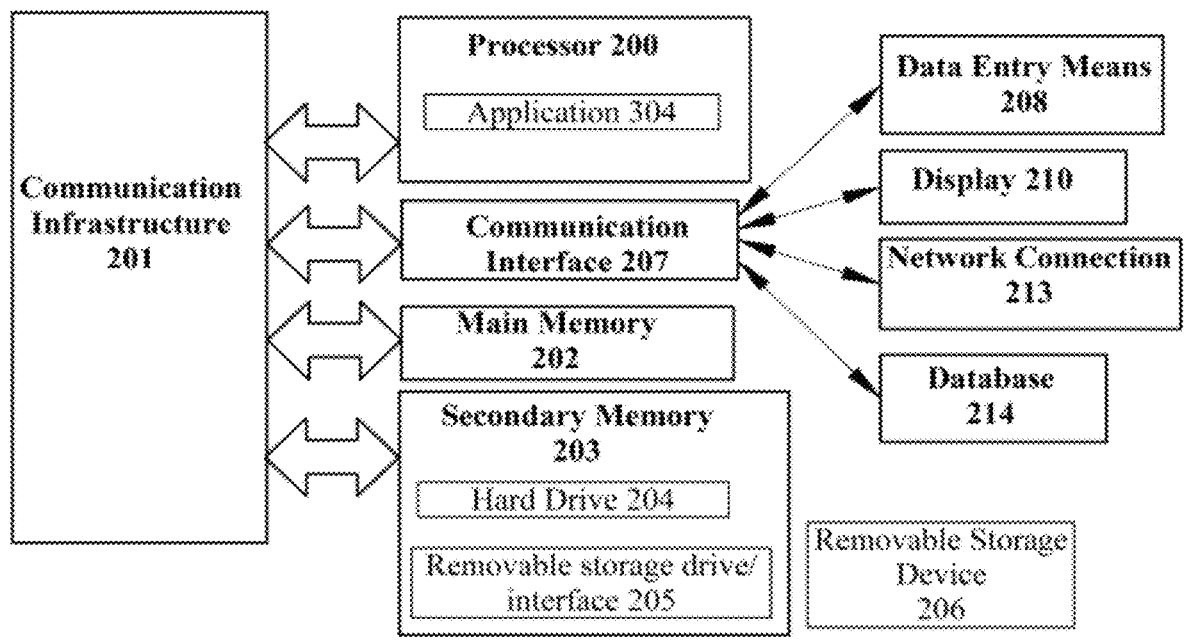
FIG. 3 is a schematic diagram depicting an example of an electronic device as described herein.

High-resolution brain image pipeline technique. The system and method disclosed herein could be better understood in light of the following observations concerning the electronic devices that support the disclosed application, and concerning the nature of applications in general. An exemplary electronic device is illustrated by FIG. 3. The processor 200 may be a special purpose or a general-purpose processor device. As will be appreciated by persons skilled in the relevant art, the processor device 200 may also be a single processor in a multi-core/multiprocessor system, such system operating alone, or in a cluster of computing devices operating in a cluster or server farm. The processor 200 is connected to a communication infrastructure 201, for example, a bus, message queue, network, or multi-core message-passing scheme.

The electronic device also includes a main memory 202, such as random access memory (RAM), and may also include a secondary memory 203. Secondary memory 203 may include, for example, a hard disk drive 204, a removable storage drive or interface 205, connected to a removable storage unit 206, or other similar means. As will be appreciated by persons skilled in the relevant art, a removable storage unit 206 includes a computer usable storage medium having stored therein computer software and/or data. Examples of additional means creating secondary memory 203 may include a program cartridge and cartridge interface (such as that found in video game devices), a removable memory chip (such as an EPROM, or PROM) and associated socket, and other removable storage units 206 and interfaces 205 which allow software and data to be transferred from the removable storage unit 206 to the computer system.

The electronic device may also include a communications interface 207. The communications interface 207 allows software and data to be transferred between the electronic device and external devices. The communications interface 207 may include a modem, a network interface (such as an Ethernet card), a communications port, a PCMCIA slot and card, or other means to couple the electronic device to external devices. Software and data transferred via the communications interface 207 may be in the form of signals, which may be electronic, electromagnetic, optical, or other signals capable of being received by the communications interface 207. These signals may be provided to the communications interface 207 via wire or cable, fiber optics, a phone line, a cellular phone link, and radio frequency link or other communications channels. The communications interface in the system embodiments discussed herein facilitates the coupling of the electronic device with data entry devices 208, the device's display 210, and network connections, whether wired or wireless 213. It should be noted that each of these means may be embedded in the device itself, attached via a port, or tethered using a wireless technology such as Bluetooth®.

Computer programs (also called computer control logic) are stored in main memory 202 and/or secondary memory 203. Computer programs may also be received via the communications interface 207. Such computer programs, when executed, enable the processor device 200 to implement the system embodiments discussed below. Accordingly, such computer programs represent controllers of the system. Where embodiments are implemented using software, the software may be stored in a computer program product and loaded into the electronic device using a removable storage drive or interface 205, a hard disk drive 204, or a communications interface 207.

The electronic device may also store data in database 212 accessible to the device. A database 212 is any structured collection of data. As used herein, databases can include "NoSQL" data stores, which store data in a few key-value structures such as arrays for rapid retrieval using a known set of keys (e.g. array indices). Another possibility is a relational database, which can divide the data stored into fields representing useful categories of data. As a result, a stored data record can be quickly retrieved using any known portion of the data that has been stored in that record by searching within that known datum's category within the database 212, and can be accessed by more complex queries, using languages such as Structured Query Language, which retrieve data based on limiting values passed as parameters and relationships between the data being retrieved. More specialized queries, such as image and metadata matching queries, may also be used to search some databases. A database can be created in any digital memory.

Persons skilled in the relevant art will also be aware that while any device must necessarily comprise facilities to perform the functions of a processor 200, a communication infrastructure 201, at least a main memory 202, and usually a communications interface 207, not all devices will necessarily house these facilities separately. For instance, in some forms of electronic devices as defined above, processing 200 and memory 202 could be distributed through the same hardware device, as in a neural net, and thus the communications infrastructure 201 could be a property of the configuration of that particular hardware device. Many devices do practice a physical division of tasks as set forth above, however, and practitioners skilled in the art will understand the conceptual separation of tasks as applicable even where physical components are merged.

Figure 4:
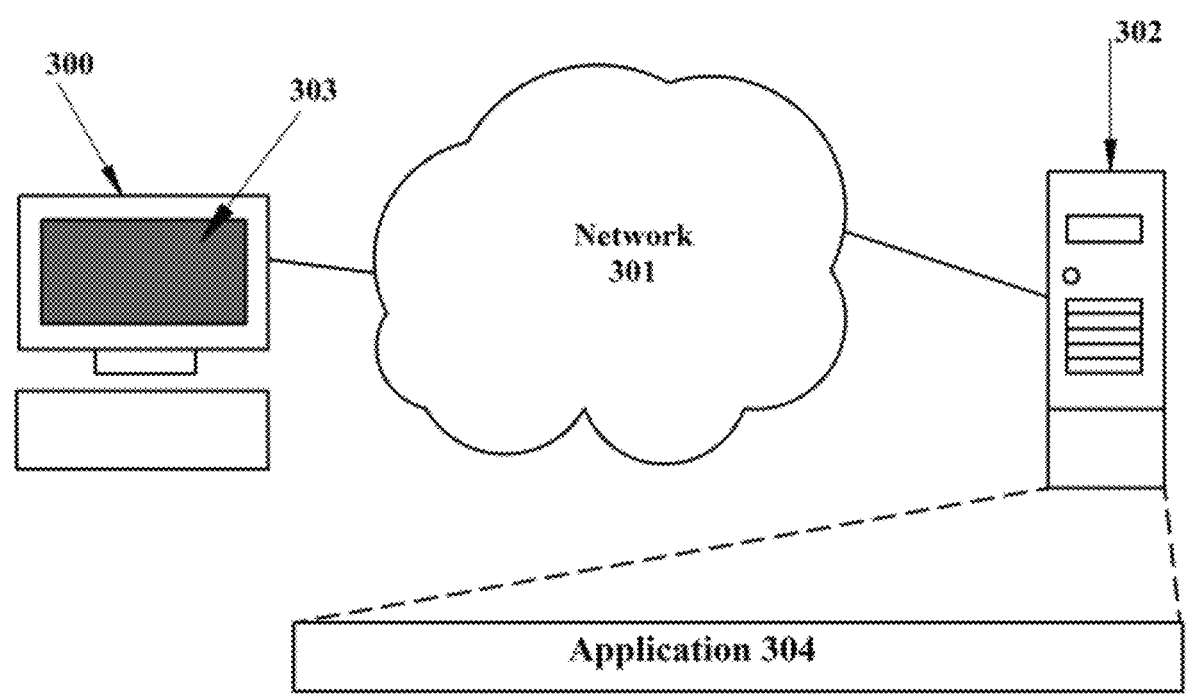
FIG. 4 is a schematic diagram of a network-based platform, as disclosed herein.

The systems may be deployed in a number of ways, including on a stand-alone electronic device, a set of electronic devices working together in a network, or a web application. Persons of ordinary skill in the art will recognize a web application as a particular kind of computer program system designed to function across a network, such as the Internet. A schematic illustration of a web application platform is provided in FIG. 4. Web application platforms typically include at least one client device 300, which is an electronic device as described above. The client device 300 connects via some form of network connection to a network 301, such as the Internet. The network 301 may be any arrangement that links together electronic devices 300, 302, and includes without limitation local and international wired networks including telephone, cable, and fiber-optic networks, wireless networks that exchange information using signals of electromagnetic radiation, including cellular communication and data networks, and any combination of those wired and wireless networks. Also connected to the network 301 is at least one server device 302, which is also an electronic device as described above. Of course, practitioners of ordinary skill in the relevant art will recognize that a web application can, and typically does, run on several server devices 302 and a vast and continuously changing population of client devices 300. Computer programs on both the client device 300 and the server device 302 configure both devices to perform the functions required of the web application 304. Web applications 304 can be designed so that the bulk of their processing tasks are accomplished by the server device 302, as configured to perform those tasks by its web application program, or alternatively by the client device 300. However, the web application must inherently involve some programming on each device.

In some aspects, the system and method described herein permit the creation of a patient-specific digital brain atlas. The atlas may be tailored, by the choice of images included in its composition, to the specific needs of a patient based upon the current clinical situation. Thus, detailed images of the patient's cerebral arteries and veins can be included to ensure the safe implantation of a DBS electrode. Other images can be included that make it easier to identify and target particular anatomic features for an operation. A database of images of all kinds from various other brains makes it possible to enhance the patient-specific atlas with images of structural and functional related such as, but not limited to, positron emission tomography (PET), functional MRI (fMRI), Single-photon emission computed tomography (SPECT) scans of brains belonging to other patients, thereby augmenting the patient data. The database images also make it possible to compensate for the unavailability of certain images of the patient brain.

Figure 5:
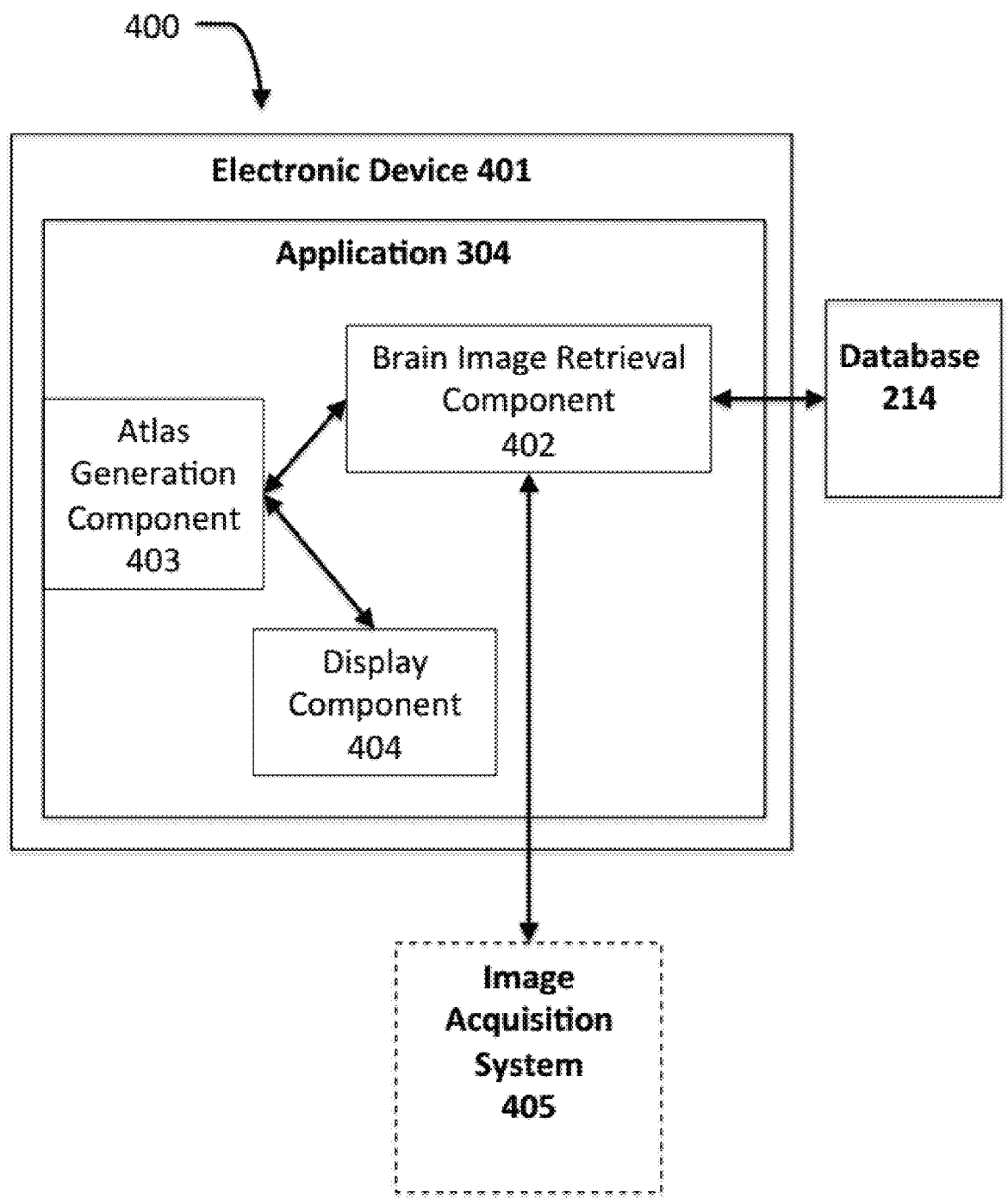
FIG. 5 is a block diagram depicting one embodiment of the disclosed system.

FIG. 5 illustrates some embodiments of the disclosed system 400. The first element is at least one electronic device 401. The electronic device 401 may be an electronic device as disclosed above in reference to FIGS. 2 and 3. The electronic device 401 may be a set of electronic devices working together as disclosed above in reference to FIGS. 3 and 4. The electronic device is programmed or configured to perform the tasks of an application 304. The application 304 may be composed of one or more a computer programs as described above in reference to FIGS. 3 and 4. The tasks the application 304 performs may be conceptually divided into a brain image retrieval component 402, an atlas generation component 403, and a display component 404. The organization of tasks into those three components solely reflects a categorization of the tasks to be performed, and does not dictate the architecture of particular implementations of the system 400.

The brain image retrieval component 402 acquires two and/or three-dimensional brain images to be used by the system. In some embodiments, the brain image retrieval component 402 communicates with an image acquisition system 405. An image acquisition system 405 is a machine that acquires image data by scanning a patient's brain, capturing the results of the scan, translating those results into a digital record, and making that digital record available to other devices, such as the electronic device 401. The image acquisition system 405 may be any system capable of rendering an image of at least a part of a brain. In some embodiments, the image acquisition system 405 includes a magnetic resonance (MR) scanner. The image acquisition system 405 in some embodiments includes a computed tomography (CT) scanner. In some embodiments, the image acquisition system 405 includes a positron emission tomography (PET) scanner. In other embodiments the image acquisition system 405 includes an ultrasound scanner. The image acquisition system 405 may also include a high-frequency ultrasound (HIFU) scanner. The image acquisition system 405 may include an optical coherence tomography (OCT) scanner. In some embodiments, the image acquisition system 405 includes an intravascular ultrasound system (IVUS). According to other embodiments, the image acquisition system 405 includes a single photon emission computed tomography (SPECT) system. Other embodiments of the image acquisition system 405 include a planar gamma scintigraphy system.

The brain image retrieval component 402 in some embodiments retrieves brain image data from memory accessible to the electronic device 401. In some embodiments, the brain image retrieval component 402 communicates with a database 213 accessible to the electronic device 401. The database 213 may contain images produced by any kind of imaging technology and protocol as described above in relation to the image acquisition system 405 above. The database 213 may contain any combination of images as described above in relation to the image acquisition system 405. The database 213 may also contain meta data such as sex, age, and health records.

The system 400 also includes an atlas generation component 403, which executes on the electronic device 401 and combines entire retrieved images or parts of retrieved images together to create a patient-specific atlas as set forth in more detail below in reference to FIG. 1.

The system 400 also includes a display component 404, which executes on the electronic device 401 and displays the patient-specific atlas. The display component 404 in some embodiments communicates with a display 210 coupled to the electronic device. In some embodiments, the display 210 is a monitor. In some embodiments, the display component 404 communicates with a computer-assisted surgery user interface system, such as the ZEUS® Surgical System, which allows a surgeon to perform surgical procedures using robot arms, and to view progress of the surgery on a display 210 which is also under the surgeon's control. In some embodiments, the display component 404 communicates with clinical instruments used for surgical planning. In some embodiments, the display component 404 communicates with systems used for post-operative programming in deep brain stimulation.

The brain image retrieval component 402 receives other forms of images in addition to MR images, in some embodiments. According to one embodiment, at least one image in the set of brain images comprises a computed tomography (CT) image. In other embodiments at least one image in the set of brain images comprises a positron emission tomography (PET) image. According to still other embodiments, at least one image in the set of brain images comprises an image of the arteries in the depicted brain. In some embodiments, the image of the arteries comprises time-of-flight magnetic resonance angiography of the arteries. At least one image in the set of brain images shows the veins in the depicted brain, according to one embodiment. In one embodiment, the image of the veins comprises a T2-star gradient-echo image of the veins. In another embodiment, at least one image in the set of brain images is an ultrasound image. In some embodiments at least one image in the set of brain images is a HIFU image. In other embodiments, at least one image in the set of brain images is an OCT image. In other embodiments, at least one image in the set of brain images is an IVUS image. According to other embodiments, at least one image in the set of brain images is a SPECT image. At least one image is a planar gamma scintigraphy image in some embodiments.

Some embodiments involve maintaining, by the electronic device, a database of brain images, and retrieving the at least one additional brain image from that database. In some embodiments, the images in the database comprise any images as described above. In some embodiments, the images in the database are organized according to the brains they represent. In some embodiments, the images corresponding to each depicted brain are combined to form a 3-dimensional atlas, according to methods described in more detail below. In some embodiments, the database contains images belonging to at least two image types, and retrieving the brain image from the database further comprises determining which image type will produce the best patient-specific atlas for the intended clinical purpose, and retrieving an image belonging to that image type from the database. An "image type," as used herein is the category of image produced by a particular imaging technique. For instance, one image type is an fMRI image, and another image type is a T1-weighted image. In some embodiments, parts of each image type are combined. In some embodiments, the entire image types are combined. In some embodiments, a particular feature or region of the brain of the patient which is not clearly visible in the image of the brain of the patient will be at its most visible if the patient-specific atlas is created, as set forth in more detail below, to contain an image from the database belonging to a particular image type likely to emphasize the missing feature or region. All image types described above in reference to this step may be included in the database, including without limitation T1, T2, SWI, FMRI, and DWI images taken with high or low intensity magnetic fields. Post-implantation images of the brains depicted in the database, as set forth in more detail below regarding the patient's brain, may also be included.

In some embodiments, the brain image retrieval component 402 retrieves an image from the database by maintaining patient information concerning the patient brain image, maintaining patient information concerning each image maintained in the database, and retrieving an image from the database having patient information matching the patient information concerning the patient brain image. In some embodiments, the patient information concerning the patient brain image and the database image is demographic information. The demographic information may be the age of the person whose brain is in the image. The demographic information may be the sex of the person whose brain is in the image. The patient information in some embodiments comprises measurement data concerning the depicted brains. In some embodiments, the measurement data describes the size of the depicted brain. In other embodiments, the measurement data describes the dimensions of a feature of the depicted brain. For example, patient data recorded concerning a particular brain may describe the dimensions of a ventricle. The patient information in some embodiments is medical history data. The medical history data may include a diagnosis of a particular illness. The illness diagnosed may be one that affects the form of the imaged brain. The diagnosis may also describe the degree of progression of the illness. The diagnosis may describe particular features in the imaged brain that correspond to the illness. The medical history data may also describe treatment history. Treatment history may include procedures attempted in the course of treatment. Treatment history may also include the outcome of attempted procedures. The patient information in some embodiments is data concerning the images taken. The data may include the image types taken; for instance, the data may indicate that a given person's brain was imaged using several MR types and a PET scan. The data may indicate the resolution level of the images taken. The data may also describe the acquisition parameters used in acquiring the image.

The matching process in some embodiments involves searching for several items of patient information in succession. For example, the brain image retrieval component 402 may first search for all images in the database corresponding to persons in the same age range as the patient, and then search within that result set for all images corresponding to persons suffering from the same illness as the patient. That result set in turn may be further searched for image types likely to compliment the images available of the patient's brain. In some embodiments, the search includes using images in the database of the same type as those used for images of the patient; for example, if the patient data includes 1.5 Tesla (or 3 Tesla) MRI, the search may be based on looking for matching 1.5 Tesla (or 3 Tesla) MRI images in the database.

Images in the database may be registered using linear and non-linear methods to a coordinate system. The coordinate system may be that of the patient images. The coordinate system may be that of the database image. The coordinate system may be dictated by the surgical procedure. The registration may be linear, meaning that the registration process subjects the image to be registered to a mapping that may be described using a system of linear transformations. Linear transformations may include translations. Linear translations may include scaling of the overall image. Linear translations may include rotations of the image. Linear transformations might include affine registration. The registration may be non-rigid, meaning that it cannot be described in terms of a system of linear equations, and that it does not necessarily preserve the proportions of the original image. A non-rigid registration process may subject different portions of the image to different linear transformations, with interpolation between regions to maintain overall image integrity. A non-rigid registration process may subject the image to elastic deformation. Non-rigid transformations may be used to line up features or landmarks in the image being registered with similar features of other images. The landmarks may be user provided. The landmarks may be anatomical. The landmarks may be automatically discovered; for example, a landmark may be discovered by an automatic sulci detection procedure. The registration may be a combination of linear and non-rigid registrations; for example, the linear registration may be used initially to place the image within the coordinate system with the appropriate orientation, and a non-rigid registration may follow to align certain features of the image with a standard location. The linear registration can also be used to select a subset of the database for future non-linear registration. The registration may be user-guided. In some embodiments, a user directs the electronic device to rotate the image within the coordinate system. In some embodiments, a user directs the electronic device to change the size of the image within the coordinate system. In some embodiments, a user directs the electronic device to align at least one feature of the imaged brain with the feature of another imaged brain. The registration may involve a combination of automated and manual processes. For instance, the registration of one image may automatically be modified to line up certain features of the image with those of another image, subsequent to which the user may direct the electronic device to make further linear or non-rigid registration modifications to line the images up to the satisfaction of the user. The registration can be done to minimize a cost, such as the mean squared error or the mutual information. The registration can be performed with existing algorithms or with tailored techniques.

In some embodiments, the brain image retrieval component 402 retrieves an image from the database by locating an image in the database that matches the patient image and retrieving the matching image. In some embodiments, the matching is determined by those images in the database minimizing a given cost among all the images of the same modality and contrast in the database. In some embodiments, the cost is computed only in regions of interest. In some embodiments the cost is computed for different modalities and contrasts independently, and for each one the minimizing image is selected. In some embodiments, the image selection is based on a linear registration. In some embodiments the image selection is based on a non-linear registration. In some embodiments the image selection is based on a combination of linear and non-linear registration. In some embodiments, the brain image retrieval component 402 locates a brain image having a feature that matches an analogous feature of the patient's brain. For instance, the brain image retrieval component 402 may locate an image having a ventricle substantially the same size and shape as a ventricle in the patient's brain. The brain image retrieval component 402 may locate an image having several features that are substantially the same as their analogous features in the patient's brain. The brain image retrieval component 402 may also perform this image-matching search within a result set of an earlier search for images whose patient information matches the patient information of the patient's image. The brain image retrieval component can produce more than one matching result. In some embodiments, all the data corresponding to the same subject in the database is used for the patient specific atlas even if the search used a subset of it for matching. In some embodiments, different images from the patient is be used to search the database. For example, a T1-weighted image of the patient's brain may be used to search for the best matching T1-weighted image, while a T2-weighted image of the patient's brain may be used to search for the best matching T2.

In other embodiments, retrieving the brain image from the database further comprises receiving, by the at least one electronic device, an instruction specifying a particular image in the database and retrieving the specified image. In some embodiments, a user enters the instruction through a user interface. The user interface may allow the user to view images from the database on the screen and select an image to combine with the patient image. The user interface may allow the user to view several images from the database in combination, and select that combination to combine with the patient image. The user may use the user interface to view images in a patient information matching result set. The user may use the user interface to view images in an image matching result set. The user may enter these directions using any form of manual data entry devices. The user interface in some embodiments is customized. In some embodiments, the user interface is one of the existing surgical platforms.

In addition, the method 100 includes merging, by the electronic device, the patient brain image with the at least one additional brain image to produce a patient-specific atlas (102). In some embodiments, where both the patient image and the at least one additional brain image are registered to the same coordinate system, the atlas generation component 403 may merge two images by superimposing one over the other in the same coordinate system. The merging process in some embodiments involves modifying the registration of one image to match it to another image. The registration modification may be automated. In some embodiments, the automated registration modification involves detecting a difference in orientation between the two images and subjecting one image to a linear transformation to rotate the image. In some embodiments, the automated registration modification involves detecting a difference in scale between the two images and subjecting one image to a linear transformation to scale the image. In some embodiments, the automated registration modification involves detecting a difference in size between the two images and subjecting one image to a linear transformation to scale the image. In some embodiments, the automated registration modification involves detecting a difference in resolution between the two images and subjecting one image to a linear transformation to scale the image. In some embodiments, the automated registration modification involves detecting a difference in position between the two images and subjecting one image to a linear transformation to move the image. In other embodiments, the automated registration modification involves detecting a difference in orientation between the two images and subjecting one image to a non-rigid transformation to match it to the other image. The non-rigid transformation may be guided by detection and matching of at least one anatomical feature present in both images.

The registration modification may be manual. In some embodiments, a user directs the electronic device to rotate the image within the coordinate system. In some embodiments, a user directs the electronic device to change the size of the image within the coordinate system. In some embodiments, a user directs the electronic device to align at least one feature of the imaged brain with the feature of another imaged brain. The registration modification may involve a combination of automated and manual processes. For instance, the registration of one image may automatically be modified to line up certain features of the image with those of another image, subsequent to which the user may direct the electronic device to make further linear or non-rigid registration modifications to line the images up to the satisfaction of the user. The user may enter these directions using any form of manual data entry devices.

Figure 6:
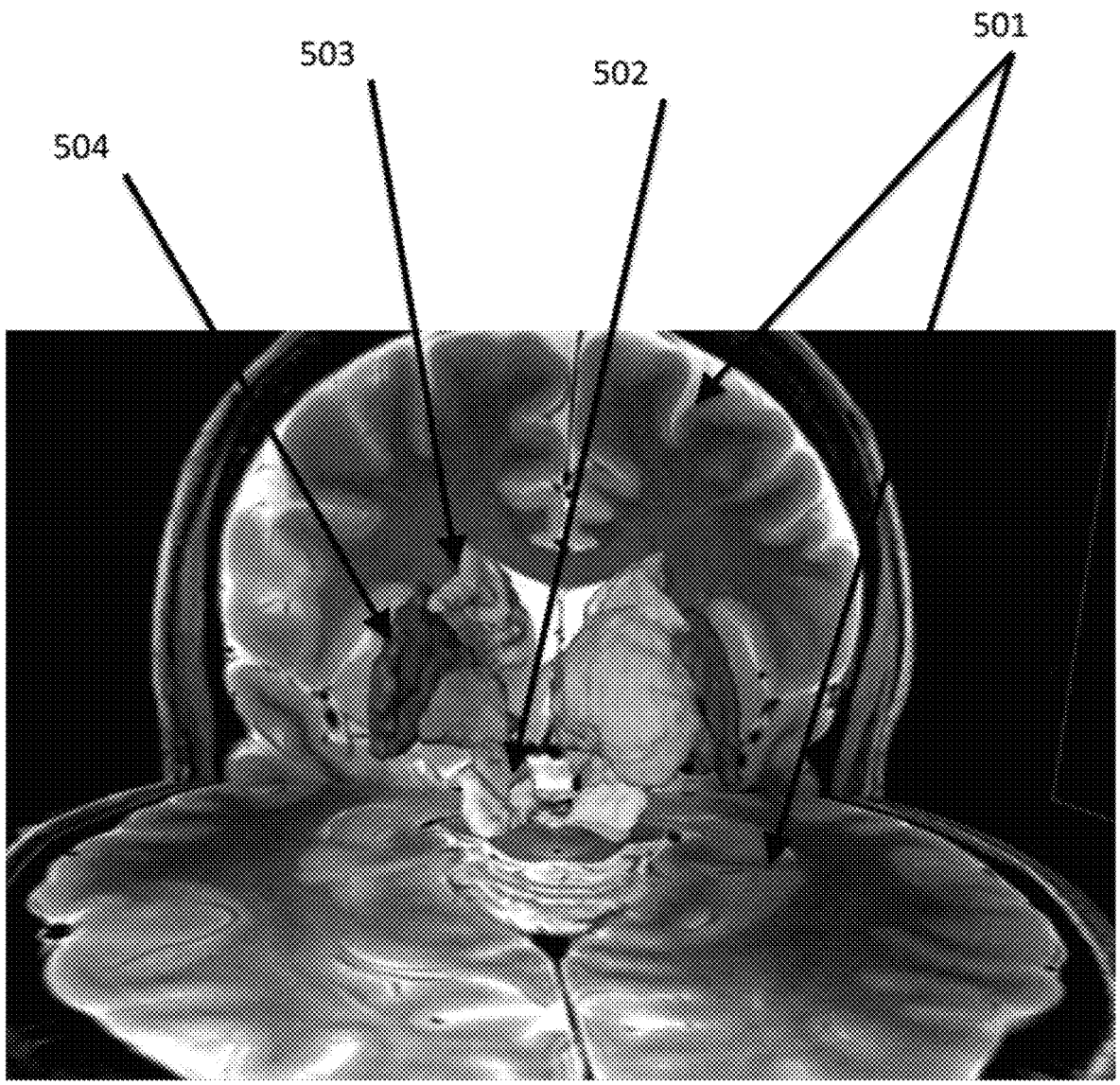
FIG. 6 depicts a possible portrayal of a patient's brain for target acquisition, with targeted anatomical structures emphasized.

In some embodiments, the atlas generation component 403 identifies particular features of the depicted brain. In some embodiments, the atlas generation component records the set of voxels corresponding to identified features or regions, and incorporates that information into the patient-specific atlas or patient-specific clinical images. In some embodiments, the atlas generation component 403 augments the patient-specific data by selecting at least one of the images in the set of brain images, identifying a region of interest in the at least one selected image, and removing all image data except the region of interest from the at least one selected image. For example, the atlas generation component 403 may, after registering an image from the database to the patient image, eliminate all but the STN or relevant shapes from the database image, and combine only the image as so modified with the patient image to produce the patient-specific atlas. FIG. 6 shows an image created by emphasizing certain structures of the brain. Most of the brain in the displayed image is limited to two cross-sectional flat views 501 behind and below the regions of interest. Rendered in three dimensions are areas of interest, which include the STN 502, the Caudate Nucleus 503, and the Putamen 504. As the rest of the three-dimensional structure of the brain is invisible in this image, the area of interest is clearly visible from the image's viewing angle.

Referring again to FIG. 1, the method 100 also includes displaying, by the electronic device, the patient-specific atlas (103). In some embodiments, the display component 404 projects the patient-specific atlas onto a two-dimensional display available to the electronic device 401 in such a way as to simulate viewing the depicted brain from a particular angle. According to some embodiments, the display component 404 identifies a region of interest in the patient-specific atlas, and emphasizes that region of interest in the displayed atlas, as depicted in FIG. 6. In some embodiments, the projection provides a view of a particular structure within the depicted brain; for example, the two-dimensional projection represented by FIG. 6 provides a view from a particular angle of the STN 502 as examples of shape of interest. In some embodiments, the projection provides a view of more than one structure within the depicted brain. In some embodiments, each anatomical feature depicted is displayed with a different color to distinguish it from the other depicted anatomical features (not shown). For instance, the STN 502 or particular shape of interest may be displayed in yellow, while the caudate nucleus 503 may be displayed in turquois or any color useful for the practitioner. In some embodiments, the user can enter instructions directing the display component 404 to change the view angle shown by the projection. In some embodiments, the display component 404 receives instructions directing it to display particular anatomical features. In some embodiments, the display component 404 receives instructions directing it to portray a particular anatomical feature in a particular color. In some embodiments, the display component 404 displays a surgical target. The surgical target may be displayed in a distinct color to contrast with its surroundings. In some embodiments, the display component 404 displays a path to a surgical target. The path in some embodiments is computed to avoid damaging blood vessels. The path in some embodiments is computed to avoid damaging neuro-anatomy.

Figure 7:
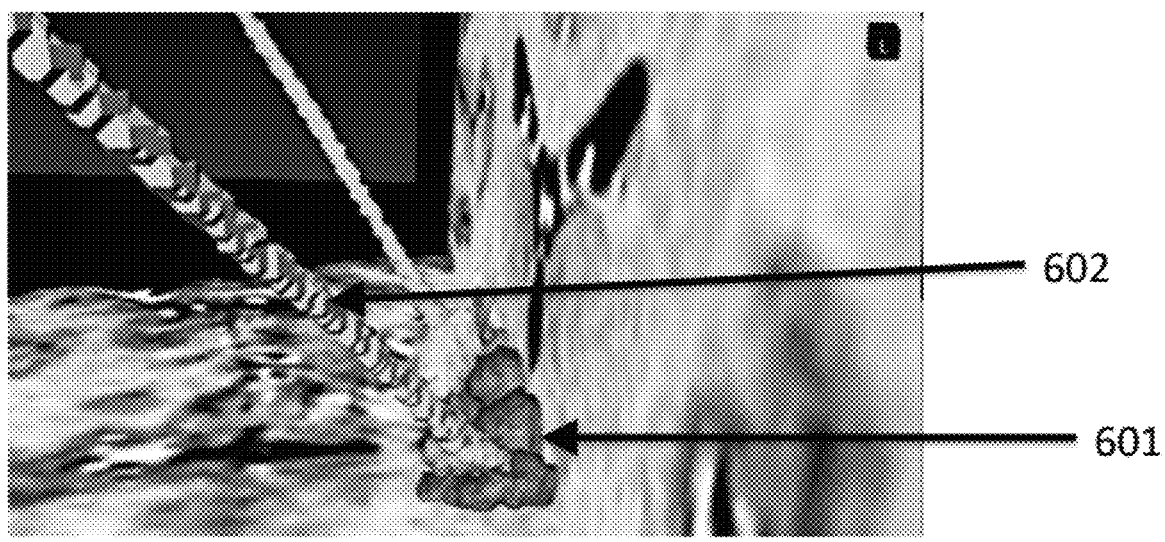
FIG. 7 depicts another possible portrayal of a patient's brain for target acquisition, with targeted anatomical structures emphasized and a path for implantation depicted.

Some embodiments of the method involve locating a target for a medical procedure. As an example, the depiction of the STN 502 in FIG. 6 may be one view used to target the STN 502 for a medical procedure. In some embodiments, the procedure is a surgical procedure. In some embodiments, the display component 404 displays a target for a surgical procedure, prior to the procedure. In some embodiments, the display component 404 displays a path for a surgical procedure to follow to arrive at the target, prior to the procedure. For example, the image in FIG. 7 depicts an anatomical target 601 for a DBS electrode insertion, as well as a path 602 for the insertion of the electrode insertion to follow. The display component 404 in some embodiments periodically displays updated images of the target during surgery. In some embodiments, the display component 404 periodically displays updated images of the path during surgery. In some embodiments, the display component 404 continuously displays updated images of the target during surgery. In some embodiments, the display component 404 continuously displays updated images of the path during surgery. In some embodiments, the display component 404 displays images to compliment endoscopic images used in endoscopic procedures. In some embodiments, the display component 404 displays images to assist in laparoscopic surgery. In some embodiments, the display component 404 produces images to aid in endovascular image-guided procedures. The display component 404 in some embodiments provides imagery to guide robotic surgery. Robotic surgery in some embodiments is a procedure in which a surgeon controls some surgical tools indirectly by manipulating data entry devices coupled to an electronic device that directly controls the surgical tools. In some embodiments, robotic surgery incorporates a display that shows the surgeon what is taking place at the site of the operation and in the surrounding anatomy.

The procedure may involve implanting a substance within the patient's brain. In some embodiments, the substance implanted in the patient's brain is living tissue. In some embodiments, the substance implanted in the patient's brain comprises one or more living cells. In some embodiments, the substance implanted in the patient's brain is genetic material. The genetic material may be placed directly in cells within the patient's brain. The genetic material may be delivered to the patient's brain by an intermediary agent. The intermediary agent may be a machine. The intermediary agent may be a small robotic device such as a "nanobot." The intermediary agent may function autonomously. The intermediary agent may be a living organism. The intermediary agent may be a prokaryotic single-celled organism. The intermediary agent may be a virus. The intermediary agent may be a eukaryotic single-celled organism. The intermediary agent may be a multicellular organism. The intermediary agent may be a chemical compound. The intermediary agent may be a protein. The intermediary agent may be a set of proteins. In some embodiments, the implantation procedure is a procedure to insert stem cells. In some embodiments, the procedure may involve placing an implant within the patient's brain. The display component 404 in some embodiments produces an image showing the implantation target within the patient's brain prior to implantation. The display component 404 in some embodiments produces an image showing the implantation path within the patient's brain prior to implantation. In some embodiments, the display component 404 periodically displays updated images of the implantation target during implantation. In some embodiments, the display component 404 periodically displays updated images of the implantation path during implantation. In some embodiments, the display component 404 continuously displays updated images of the implantation target during implantation. In some embodiments, the display component 404 continuously displays updated images of the implantation path during implantation. In some embodiments, the implantation procedure is a procedure to insert a DBS electrode and lead.

Figure 8:
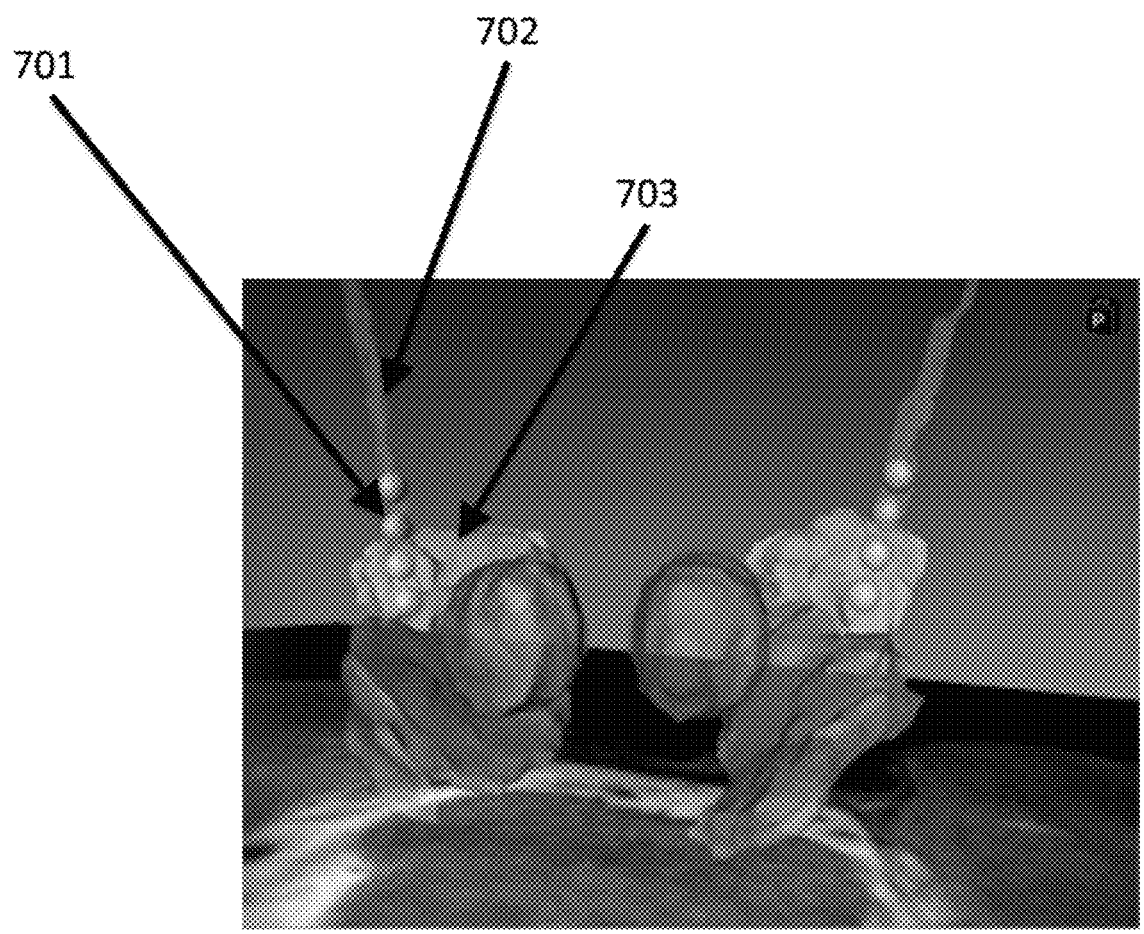
FIG. 8 shows a possible portrayal of a patient's brain after implantation of a DB S electrode, emphasizing the affected anatomical structures and the location of the electrode itself.

In some embodiments, the method further comprises receiving at least one post-implantation image showing the brain of the patient after the insertion of an implant, merging the post-implantation image with the patient-specific constructed atlas to form a post-implantation composite image, and displaying the post-implantation composite image. The implant may be any foreign object inserted wholly or partially into the brain. Implants may include, without limitation, DB S electrodes, DBS leads, microchips, electrodes for interfacing with neurons, radio frequency transmitters, radio frequency receivers, neural implants for sensory substitution, and auditory brainstem implants. The post-implantation image may be a CT image. The post-implantation image may be any other medical image as described above in reference to FIG. 4. In some embodiments, the atlas generation component 403 combines the post-implantation image with the patient-specific atlas using the techniques set forth above in reference to step 102. In some embodiments, the atlas generation component 403 creates the combination image by registering the post-implantation image with any of the pre-implantation patient data. In some embodiments, the atlas generation component 403 creates the combination image by registering the post-implantation image with the corresponding patient-specific atlas does such combination. In some embodiments, the displayed electrode position is used to guide efforts to reposition the implant. In some embodiments, real-time CT imaging is combined with the patient-specific atlas to guide the initial insertion and repositioning of an implant. In some embodiments, the displayed electrode position is used to aid in programming an electrode to determine the most relevant electrode contact/contacts for optimal benefits of the DBS. FIG. 8 depicts a combination image that could be generated by one embodiment, superimposing the captured location of a DBS electrode 701 and lead 702 over an image of the patient's STN (or the corresponding one from the atlas) 703 into which the electrode 701 has been implanted.

In some embodiments, the display component 404 displays a target for procedures that exchange energy with the patient's brain without implantation. In some embodiments, the display component 404 displays a target for radiation therapy; for example, the display component 404 may display a tumor for radiation therapy to target. In some embodiments, the display component 404 displays a target for radiosurgery. Radiosurgery may involve a small number of discrete doses of radiation stereotactically focused on a specific target within the patient's brain. In some embodiments, the display component 404 displays a target for focused ultrasound surgery. Focused ultrasound surgery, in some embodiments, uses a high-intensity, focused ultrasound beam to destroy targeted tissue.

Embodiments of the disclosed systems and methods enable neurosurgeons to engage in far more sophisticated and accurate surgery and DBS implantation procedures. In particular, the ability to avoid blood vessels and vital neural structures, and to select a more accurate initial target and path for DBS implantation, will have the potential to reduce the time required for DBS implantation, as well as the rate of complications. The system and methods disclosed will enhance the ability to engage in automated procedures such as robotic surgery. In such a scenario, the patient specific atlas may dictate to the robotic system the target and the entire penetration path. Tele-surgery will also benefit from the use of higher-quality, more flexible imaging techniques. The ability to improve depiction of difficult-to-image tissues such as white matter will enable neurosurgeons to target tissues previously out of reach.

STN location prediction method.

The preprocessing. Sub-cortical structures—SN, red nucleus (RN), globus pallidus interna (GPi), and Thalamus (Tha) within the Basal ganglia and thalamus region—are chosen as potential predictors of the STN on the 7 T MRI, considering adjacency to the STN and visibility to be segmented. On the 1.5 T (or clinical) MRI data, only detectable RN structures are used as predictors of the STN (the other structures can be challenging to identify on typical clinical imaging, and could be used if identifiable).

Figure 9:
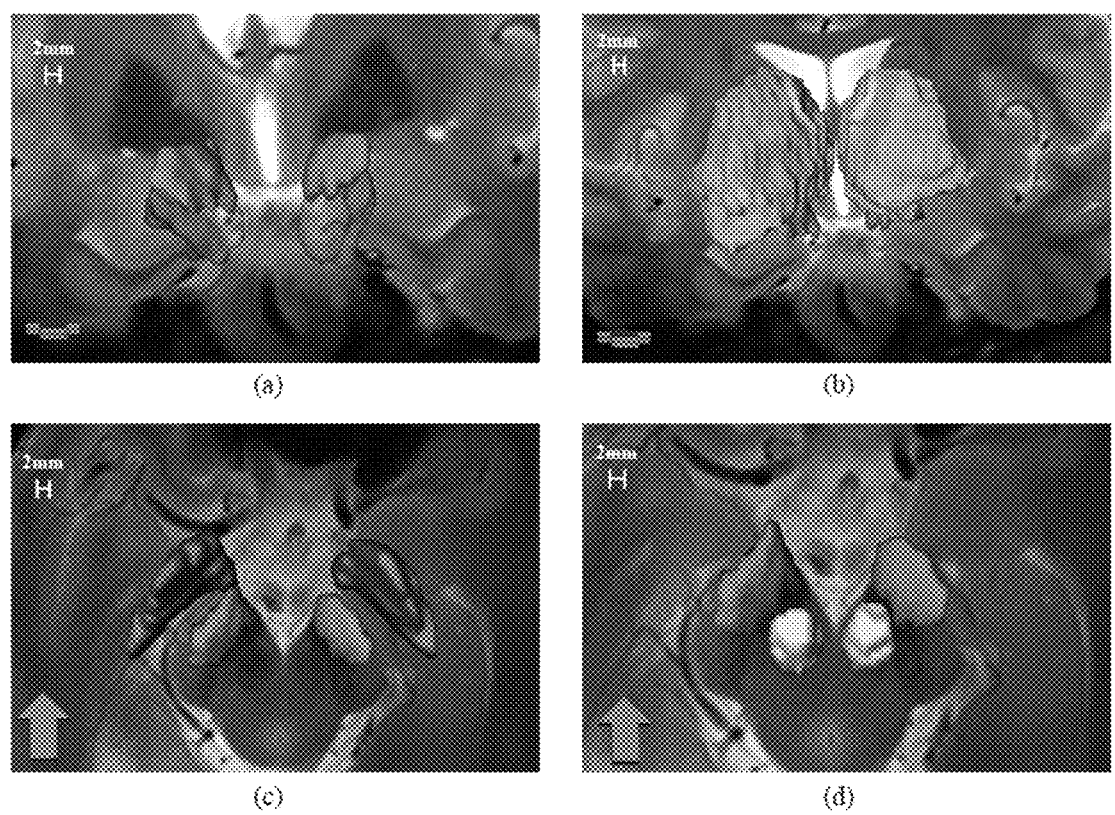
FIG. 9 shows the 3D shapes of manually segmented structures on the T2W MRI (from one subject). (a) SN and STN in the coronal direction. (b) Tha and STN in the coronal direction. (c) GPi and STN in the axial direction. (d) RN and STN in the axial direction. The red represents the STN structures. The blue, gold, green, and grey represent SN, Tha, GPi, and RN structures, respectively. Arrows are toward the anterior direction.

Left and right sides of SN, STN, RN, GPi, and Tha on the high-field (7T) MR training datasets are segmented by computer programs or anatomical experts according to the subject-specific analysis pipeline. 3D segmentation of the SN, STN, RN, GPi, and Tha in axial and coronal T2W of the 7 T MR dataset are visualized in 3D with the Amira software (Mercury Computer System) in FIG. 9, commercial or in house GUI and visualization tools can be used at this step. Since GPi, RN, and Tha were here segmented in the axial direction of the high resolution SWI and T2W, while SN and STN were segmented in the coronal direction of the high resolution SWI and T2W, SN and STN on each dataset are initially registered onto the axial SWI using FSL FLIRT (FMRIB's Linear Image Registration Tool) to transform all the structures into a common coordinate space. Other commercial or in house software packages can be used for this registration and other directions for the registration step.

For the prediction test and its validation on the clinical (1.5 T) MR datasets, the RN and STN were manually segmented on the combination of coronal SWI and T2W acquired at the corresponding 7 T MR datasets and registered onto the axial T2W data using FSL FLIRT (again other registration techniques could be used). Registered RN and STN structures were then registered onto T1W data at 1.5 T using the transformation matrix obtained by registering the axial T2W at 7 T onto the axial T1W at 1.5 T with the co-registration protocol between 7T and 1.5 T MRI. For the practical clinical case in which the 7 T MR imaging is not available, the RN structure can be automatically or manually segmented on the axial T2W acquired at 1.5 T MR test data and then registered onto 1.5 T reference data which has a pair of corresponding 7 T MR image (See FIG. 2 (b)).

It should be noted that the STN and its predictors of each training set obtained at high-field (7T) need to be normalized into the same coordinate space as the test data (7T or 1.5 T), since the pose variability (e.g., different locations and orientations of patients during the scans and the resolution disparity between different MR modalities or magnetic fields) between predictors on the test data and the 7 T MR training data might yield inaccurate prediction results. For that purpose, we normalized the coordinate space and aligned axial T2W images of 7 T MR training sets onto axial T2W images of 7 T MR test data using affine linear registration with mutual information (MI) similarity metric. STNs and its predictors on the 7 T MR training sets were then registered onto the 7 T MR test data using the obtained transformation matrix (M_(i,7T)) between 7 T MR training sets and test set (see FIG. 2(a)).

Additionally, for the prediction at 1.5 T MRI, STNs and RNs of 7 T MR training data (registered onto 7 T MR test data) and STNs and RNs manually segmented at 7 T MR test data are registered onto T1W test image at 1.5 T using the existing transformation matrix between axial T2W image at 7 T and T1W image at 1.5 T MR test set. In particular, when a 7 T corresponding pair of 1.5 T MR test data is not available, a pair of 7 T and 1.5 T MR reference data is employed. As shown in FIG. 2(b), STNs and RNs of 7 T MR training data are registered onto the 7 T MR reference data with transformation matrix (M_(i,7T)) using ANTS or any other package (commercial or in house) and then registered onto its corresponding 1.5 T MR reference data by the transformation matrix (M (7T→1.5 T)) between the two data. Therefore, STNs and RNs from 1.5 T MR test data (which has no corresponding pair of 7 T MR image), registered onto 1.5 T MR reference data using the transformation matrix (M_1.5 T), are normalized and aligned to the same coordinate space as STNs and RNs of 7 T MR training set registered onto the 1.5 T MR reference data.

Figure 10:
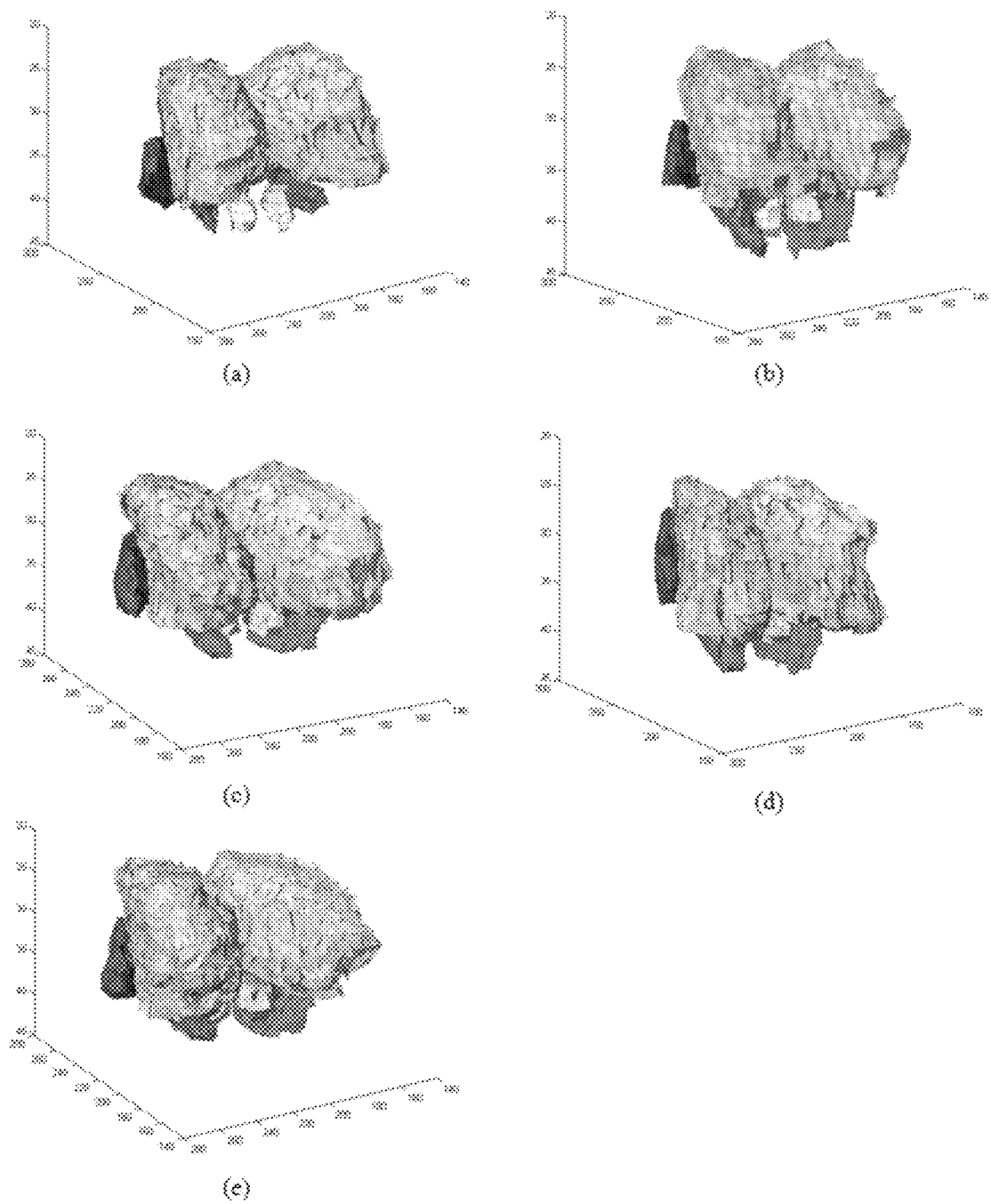
FIG. 10 shows 3D Surface and its landmark points, in correspondence, of RN, SN, STN, GPi, and Tha from training data 1 (a) to 5 (e) in the coordinate space. The gray, blue, red, green, and yellow represent RN, SN, STN, GPi, and Tha structures, respectively. The small black dots distributed along the surfaces of each structure are surface landmark points.

Statistical Shape Models. Statistical shape models enable us to exploit prior information about shape variations of anatomical structures from a set of training shapes. Common statistical shape models are based on a point distribution model (PDM) which represents a shape by a set of landmark points (i.e., vertices in a mesh) distributed along its surface, and models the shape variation. Particularly, the correspondence among landmark points of training shapes is required in order to capture variations of each shape and build a regression model for shape prediction. A minimum description length (MDL) based approach has been recognized as an effective shape correspondence method. To obtain such landmarks in correspondence across a set of training shapes, we adopt an MDL-based method that first generates landmarks by a conformal mapping of a spherical mesh parameterization to training shapes, and then optimizes the correspondence by applying the gradient descent algorithm. 3D shapes of SN, STN, RN, GPi, and Tha (remember that we use these important structures as examples of the invention, the technique applies to other regions as well) and landmark points distributed along their surfaces, in correspondence, across five 7 T MR training sets are shown in FIG. 10.

In our prediction framework, three dimensional shapes of a predictor for the STN with a set of n_"x" landmark points and the STN with a set of n_"y" landmark points, for N training sets, are represented as $\mathbbm{x}_i \in \mathbb{R}^{n_x \times 3}$ and $\mathbbm{y}_i \in \mathbb{R}^{n_y \times 3}$, $i \in \{1, \ldots, N\}$. Column vectors $x_i \in \mathbb{R}^{3n_x}$ and $y_i \in \mathbb{R}^{3n_y}$, $i \in \{1, \ldots, N\}$, are obtained by concatenating all the coordinates for the landmark points:

$$x_i = (x_{1,1}, x_{1,2}, x_{1,3}, \ldots, x_{n_x,1}, x_{n_x,2}, x_{n_x,3})^T, y_i = (y_{1,1}, y_{1,2}, y_{1,3}, \ldots, y_{n_y,1}, y_{n_y,2}, y_{n_y,3})^T \quad (1)$$

Additionally, we denote a shape of a predictor for the STN (here used as example of shape to be predicted) and the predicted STN on the real data as vectors $x^{(p)} \in \mathbb{R}^{3n_x}$ and $y^{(p)} \in \mathbb{R}^{3n_y}$, respectively. Note that we aim at estimating the shape of the STN $y^{(p)}$ from the shape of its predictor $x^{(p)}$ on the real data using the spatial relationship between the STN $\{y_i\} \in \mathbb{R}^{3n_y \times N}$ and its predictors $\{x_i\} \in \mathbb{R}^{3n_x \times N}$ across the training set.

Having registered the training datasets onto the real data, predictors for the STN on the training sets and the real data are aligned and thereby the pose variability between them can be reduced (FIGS. 2(a) and (b)). Furthermore, we can globally align surface landmark points for predictors on the training sets and real data to yield more reliable prediction of the STN. For that purpose, we perform a rigid transform or affine transform of whole surface points for the STN and its predictors on the training sets (registered onto the real data) (e.g., $\{\mathbbm{x}_i; \mathbbm{y}_i\} \in \mathbb{R}^{(n_x+n_y) \times 3}$, where i is from 2 to N) to those for one of the training sets as a reference (e.g., $\{\mathbbm{x}_1; \mathbbm{y}_1\}$ for i=1). We then apply the transformation matrix between surface points $\mathbbm{x}_1$ on the reference of the training sets and $\mathbbm{x}^{(p)}$ on the real data to aligned whole surface points for the STN and its predictors across the training datasets.

Shape parameters and poses of the STN and its predictors across the training set and predictors on the real data are obtained from their aligned surface landmark points in order to extract their spatial relationship in a lower dimensional space, as further detailed next. More specifically, the generalized Procrustes analysis is performed on each predictor of the STN $\mathbbm{x}_i$ and the STN $\mathbbm{y}_i$ with respect to their mean shapes $m\mathbbm{x}$ and $m\mathbbm{y}$, respectively, across training sets, removing poses from shapes. The alignment process yields pose parameter vectors $\{\gamma_i^x\} \in \mathbb{R}^{10 \times N}$ and $\{\gamma_i^y\} \in \mathbb{R}^{10 \times N}$ including translations $\mathbb{R} \in \mathbb{R}^3$, scaling factors $s \in \mathbb{R}^3$, and entries of a 3D rotation matrix $r \in \mathbb{R}^4$. Also, a pose parameter vector $\gamma^{x^{(P)}} \in \mathbb{R}^{10}$ for a predictor of the STN $x^{(P)}$ on the real data is calculated with respect to $m\mathbbm{x}$.

Aligned column vectors $\bar{x}_i$ and $\bar{y}_i$ for surface points in the training set are then modeled in lower dimensional space using shape parameterization methods such as principal components analysis (PCA). In this particular context, we employ as example a kernel PCA (KPCA), a non-linear extension of PCA, in order to increase the predictive potential by considering non-linear relationships between training shapes.

In KPCA, the input space (e.g., $\bar{x}_i \in \mathbb{R}^{3n_x}$) is non-linearly mapped into a high dimensional feature space $\mathcal{F}$ by $$\phi: \mathbb{R}^{3n_x} \to \mathcal{F}, \bar{x}_i \to \phi(\bar{x}_i). \qquad (2)$$

The covariance matrix C in the feature space $\mathcal{F}$ is defined as $$C = \frac{1}{N} \sum_{i=1}^{N} \tilde{\phi}(\bar{x}_i) \tilde{\phi}(\bar{x}_i)^T, \qquad (3)$$

where $\tilde{\phi}(\bar{x}_i)$ is the centered map given by $\phi(\bar{x}_i) - \bar{\phi}_x$, denoting the mean of the $\phi$ map by $$\bar{\phi}_x = \sum_{i=1}^{N} \phi(\bar{x}_i).$$

Linear PCA in the feature space $\mathcal{F}$ involves solving the eigenvalue problem $Cv^x = \lambda v^x$, where $v^x \in \mathcal{F} \setminus \{0\}$ are eigenvectors and $\lambda$ are non-zero eigenvalues of the covariance matrix C. Substituting the covariance matrix C into the eigenvalue problem, we obtain $$Cv^x = \frac{1}{N} \sum_{i=1}^{N} (\tilde{\phi}(\bar{x}_i) \cdot v^x) \tilde{\phi}(\bar{x}_i). \qquad (4)$$

As this implies that all the eigenvectors $v^x$ lie in the span of $\tilde{\phi}(\bar{x}_1), \ldots, \tilde{\phi}(\bar{x}_N)$, $v^x$ can be represented as $$v^x = \sum_{i=1}^{N} a_i \tilde{\phi}(\bar{x}_i), \qquad (5)$$

where $\alpha^i$ are coefficients for $i \in \{1, \ldots, N\}$. The equivalent eigenvalue problem is then considered as $$(\tilde{\phi}(\bar{x}_i) \cdot Cv^x) = \lambda(\tilde{\phi}(\bar{x}_i) \cdot v^x). \qquad (6)$$

Substituting (4) and (5) into (6) and introducing a centered kernel matrix $\tilde{K} \in \mathbb{R}^{N \times N}$ with entries $\tilde{\kappa}_{ij} = \tilde{k}(\bar{x}_i, \bar{x}_j)$, where $\tilde{k}(\bar{x}_i, \bar{x}_j) = (\tilde{\phi}(\bar{x}_i) \cdot \tilde{\phi}(\bar{x}_j))$ for $i,j \in \{1, \ldots, N\}$), we obtain $\tilde{K}^2 u = N\lambda \tilde{K}u$, and then arrive at its equivalent eigenvalue problem in the matrix form with $\tilde{\lambda} = N\lambda$, $$\tilde{K}U = \Lambda U, \qquad (7)$$

where $U \in \mathbb{R}^{N \times N}$ is the unitary matrix whose column vectors $u_i = [a_{i,1}, \ldots, a_{i,N}]^T$ represent eigenvectors and $\Lambda \in \mathbb{R}^{N \times N}$ is the diagonal matrix of eigenvalues $\tilde{\lambda}_i$ for $i \in \{1, \ldots, N\}$. Note that $\tilde{K}$ is calculated by HKH, where $H \in \mathbb{R}^{N \times N}$ is the matrix given by $$I - \frac{1}{N} 11^T$$

with the identity matrix $I \in \mathbb{R}^{N \times N}$ and the column vector $1 \in \mathbb{R}^{N \times 1}$ with all 1's entries, centering $K \in \mathbb{R}^{N \times N}$ with entries $\kappa_{ij} = k(\bar{x}_i, \bar{x}_j)$ where $k(\bar{x}_i, \bar{x}^j) = (\phi)(\bar{x}_i) \cdot \phi(\bar{x}_j))$ for $i,j \in \{1, \ldots, N\}$.

Here, we choose as example the commonly used Gaussian kernel $k(\bar{x}_i, \bar{x}_j) = \exp(-\|\bar{x}_i - \bar{x}_j\|^2 / 2\sigma^2)$, with a parameter a controlling the width of the kernel. The qth eigenvector of the covariance matrix C in the feature space $\mathcal{F}$ from (5) by solving the kernel eigenvalue problem of (7) can be obtained by $$v_q^x = \sum_{i=1}^{N} a_{q,i} \tilde{\phi}(\bar{x}_i), \qquad (8)$$

where $q \in \{1, \ldots, N\}$. Normalizing $v_q^x$ (i.e., $v_q^{xT} v_q^x = 1$), we obtain the qth orthonormal eigenvector $\tilde{v}_q^x$ of the covariance matrix C in the feature space as $$\tilde{v}_q^x = \sum_{i=1}^{N} \tilde{a}_{q,i} \tilde{\phi}(\bar{x}_i), \qquad (9)$$

where $\tilde{\alpha}_{q,i} = \alpha_{q,i} / \sqrt{\tilde{\lambda}_q}$. The resulting qth kernel principle components $z_{q,j}^x$ can then be calculated by projecting the $\tilde{\phi}$ map of each predictor for the STN $\bar{x}_j$ in the training set onto $$\tilde{v}_q^x as z_{q,j}^x = (\tilde{v}_q^x \cdot \tilde{\phi}(\bar{x}_j)) = \sum_{i=1}^{N} \tilde{a}_{q,i}(\tilde{\phi}(\bar{x}_i) \cdot \tilde{\phi}(\bar{x}_j)) = \sum_{i=1}^{N} \tilde{a}_{q,i} \tilde{k}(\bar{x}_i, \bar{x}_j), \qquad (10)$$

where the centered kernel vector $\tilde{k}(\bar{x}_i, \bar{x}_j)$ can be calculated from $k(\bar{x}_i, \bar{x}_j)$.

When the dimension of the feature space $\mathcal{F}$ is infinite, the eigenvalue problem on the covariance matrix C is not solvable. Kernel methods enable us to obtain the principal components in feature space without explicitly computing the $\phi$ mapping (the "kernel trick").

In the proposed prediction framework (FIG. 2(c)), kernel principle components for eigenvectors $\tilde{v}^x$ ordered by the first r largest eigenvalues $\tilde{\lambda}$ in the feature space (i.e., $r \ll N$) are stored as shape parameter vectors $\beta_i^x$ for each predictor of the STN $\bar{x}_i$ in the training set:

$$\beta_i^x = [z_{1,i}^x, \ldots, z_{r,i}^x]^T. \qquad (11)$$

Similarly, shape parameter vectors $\beta_i^y$ for each STN $\bar{y}_i$ in the training set are obtained by projecting $\tilde{\phi}(\bar{y}_i)$ onto eigenvectors $\tilde{v}^y$ ordered by the first r largest eigenvalues of the covariance matrix of $\tilde{\phi}(\bar{y}_i)$ in the feature space, $$\beta_i^y = [z_{1,i}^y, \ldots, z_{r,i}^y]^T, \qquad (12)$$

where $z_{r,i}^y = (\tilde{v}_r^y \cdot \tilde{\phi}(\bar{y}_i))$. Additionally, shape parameter vectors $\beta^{x^{(p)}}$ for a predictor of the STN on the real data can be calculated by projecting the $\tilde{\phi}$ map of the predictor vector $\bar{x}^{(p)}$ onto eigenvectors $\tilde{v}^x$ corresponding to the first r largest eigenvalues of the covariance matrix C of $\tilde{\phi}(\bar{x}_i)$, $$\beta^{x^{(p)}} = [z_1^{x^{(p)}}, \ldots, z_r^{x^{(p)}}]^T, \qquad (13)$$

where $z_r^{x^{(p)}} = (\tilde{v}_r^x \cdot \tilde{\phi}(\bar{x}^{(p)}))$.

Now let us assume that shape parameters of the STN $\beta^{y^{(p)}}$ are predicted from $\beta^{x^{(p)}}$ on the real data using the relationship between $\{\beta_i^x\}$ and $\{\beta_i^y\}$ across the training set in our prediction framework, and also pose parameters of the STN $\gamma_y^{(p)}$ are predicted from $\gamma^{x^{(p)}}$ on the real data using the relationship between $\{\gamma_i^x\}$ and $\{\gamma_i^y\}$ across the training set. We need to reconstruct the landmark points of the STN $\bar{y}^{(p)}$ in the input space from the predicted $\beta^{y^{(p)}}$ in the feature space. Finally, we obtain this way the complete shape of the STN $y^{(p)}$ from $\bar{y}^{(p)}$ with predicted pose parameters $\gamma^{y^{(p)}}$. Note that the projection of $\tilde{\phi}(\bar{y}^{(p)})$ onto the subspace spanned by the eigenvectors $\tilde{v}^y$ corresponding to the first r largest eigenvalues of the covariance matrix of $\tilde{\phi}(\bar{y}_i)$ in the feature space is given by $$\mathcal{P}\tilde{\phi}(\bar{y}^{(p)}) = \sum_{q=1}^{r} z_q^{y(p)} \tilde{v}_q^y, \quad (14)$$

where $z^{y^{(p)}}$ are r predicted principal components of $\beta^{y^{(p)}}$. Also, we obtain $$\mathcal{P}\phi(\bar{y}^{(p)}) \text{ with} \quad (15)$$

$$\bar{\phi}_y = \sum_{i=1}^{N} \phi(\bar{y}_i) \text{ as } \mathcal{P}\phi(\bar{y}^{(p)}) = \sum_{q=1}^{r} z_q^{y(p)} \tilde{v}_q^y + \bar{\phi}_y.$$

The reconstruction problem of $\bar{y}^{(p)}$ (i.e., pre-image estimation $\bar{y}_{est}^{(p)}$ in the original space, where $\phi(\bar{y}_{est}^{(p)}) \cong \mathcal{P}\phi(\bar{y}^{(p)})$) is ill-posed since the $\phi$ mapping is not invertible for non-linear kernel functions. Several studies have been proposed to address this non-linear optimization problem in KPCA proposed the iterative approach which minimizes the squared distance between $\phi(\bar{y}_{est}^{(p)})$ and $\mathcal{P}\phi(\bar{y}^{(p)})$, but suffers from local minimum and initialization problems. The pre-image can be estimated from a relationship between the feature space distance $\tilde{d}(\mathcal{P}\phi(\bar{y}^{(p)}), \phi(\bar{y}_i))$ and the corresponding distance $d(\bar{y}_{est}^{(p)}, \bar{y}_i)$ in input space, based on multidimensional scaling. However, it requires highly computational costs. More recently, the reconstruction approach which only utilizes the feature space distance without the iteration was proposed. Also, the local linear interpolation based approach only uses the input space distances between the estimated pre-image and nearest neighbors for stochastic input modeling. We here disclose a more reliable and faster reconstruction approach presented to estimate $\bar{y}^{(p)}$ in our prediction problem.

The extraction of the shape parameters (i.e., $\{\beta_i^y\}$ and $\{\beta_i^x\}$) and poses (i.e., $\{\gamma_i^y\}$ and $\{\gamma_i^x\}$) for the STNs and its predictors across the training set using a statistical shape model to capture their variation in the low dimensional space has been disclosed above.

Then the disclosed method focused on the prediction problem for the shape and pose of the STN (or other brain structures of interest) from those of its predictors on the real clinical data, this is done by investigating the relationship between shape parameters and poses, respectively, across the training set using the regression model described in the next section.

Partial Least Squares Regression Based Shape Prediction. The disclosed method further addresses the regression problem of finding the dependency between the shape parameters and poses of the STN (or shape/region to be predicted) and the shape parameters and poses of its predictors in the training set. Since the shape prediction is under-determined (i.e., low sample size and high dimensional problem), a biased linear regression is preferred, though other prediction tools can be used as well.

The disclosed method proposes in one possible embodiment utilization of the PLSR technique that has been widely applied even to the multi-collinearity problem having high correlation between either set of vectors in the training data, particularly, in under-determined system. PLSR extends the multi-linear regression and finds principal factors (i.e., latent vectors) within a set of predictors X to predict a set of response vectors Y so that the covariance between them is maximal.

In the prediction problem for the disclosed method, X contains a set of centered shape parameters $\{\tilde{\beta}_i^x\}^T$ or poses $\{\tilde{\gamma}_i^x\}^T$ for predictors of the STN and Y contains a set of centered shape parameters $\{\tilde{\beta}_i^y\}^T$ or poses $\{\tilde{\gamma}_i^y\}^T$ for the STNs in the training set, where $$\tilde{\beta}_i = \beta_i - \sum_{i=1}^{N} \beta_i \text{ and } \tilde{\gamma}_i = \gamma_i - \sum_{i=1}^{N} \gamma_i$$

are obtained by centering shape parameters $\beta_i$ and poses $\gamma_i$. When predictors consist of multiple structures, we extract pose and shape parameters for each predictor and concatenate pose and shape parameter vectors of multiple predictors, respectively, to exploit local information for pose and shape of each predictor in the prediction framework. For example, shape and pose parameter vectors for the left and right side of a predictor on the training sets are concatenated as $\tilde{\beta}_i^x = (\tilde{\beta}_{i,left}^x; \tilde{\beta}_{i,right}^x)$ and $\tilde{\gamma}_i^x = (\tilde{\gamma}_{i,left}^x; \tilde{\gamma}_{i,right}^x)$, and shape and pose parameter vectors for left and right side of a predictor on the real data are also concatenated as $\beta^{x^{(p)}} = (\beta_{left}^{x^{(p)}}; \beta_{right}^{x^{(p)}})$ and $\gamma^{x^{(p)}} = (\gamma_{left}^{x^{(p)}}; \gamma_{right}^{x^{(p)}})$.

The PLSR decomposes X and Y by finding latent matrices T and F:

$$X = TP^T, Y = FG^T \text{ with } F = TB + \varepsilon, \quad (16)$$

where P is a loading matrix of X, G is a weight matrix of Y, B is a diagonal matrix of regression weights, and $\varepsilon$ is the regression error. The latent vectors t and f of latent matrices T and F, respectively, are obtained by finding two weight vectors w and g such that linear combinations of columns of X and Y have maximum covariance, meaning that $t^T f$ is maximal:

$$t = Xw, f = Yg \text{ with } w^T w = 1, t^T t = 1. \quad (17)$$

Specifically, w and g are iteratively updated and then obtained latent vectors t and f are subtracted from X and Y, respectively, by the nonlinear iterative partial least squares approach. The iteration continues until X become a null matrix. Finally, response vectors Y are predicted as $$Y \cong TBG^T = XB_{PLS}, \quad (18)$$

where $B_{PLS} = P^{T+} BG^T$, with $P^{T+}$ the Moore-Penrose pseudo inverse of $P^T$.

Let $B_{PLS}^{\beta}$ and $B_{PLS}^{\gamma}$ be regression coefficients for shape parameters and poses, respectively, between the STN and its predictors in the training set, obtained by performing the PLSR in our prediction problem. Given shape parameters $\beta^{x^{(p)}}$ and poses $\gamma^{x^{(p)}}$ for a predictor of the STN on the real data, shape parameters $\beta^{y^{(p)}}$ and poses $\gamma^{y^{(p)}}$ for the STN on the real data are then predicted as $$\beta^{y^{(p)}} = \beta^{x^{(p)T}} B_{PLS}^{\beta}, \gamma^{y^{(p)}} = \gamma^{x^{(p)T}} B_{PLS}^{\gamma} \quad (19)$$

Neighboring Structures as Predictors of the STN. The framework for predicting shape and pose has been derived for the method disclosed. The actual shapes used by the predicting method is further disclosed below.

Prediction accuracy in the regression-based model is influenced by the degree of correlation between the STN and its predictor structures. Recent studies have reported that pairs of adjacent brain structures are highly correlated. The predictors for the STN in sub-cortical structures are introduced by considering the spatial adjacency with the STN and the visibility (easy detectable) on the real MR data (1.5 T/3 T or 7 T) from a specific subject.

The STN is a small approximately convex structure which is divided into the motor territory (as the target area for DBS surgery for Parkinson's disease for example) in the posterolateral region and the limbic territory of the anteromedial region, and is surrounded by several sub-cortical regions— zona incerta, medial lemniscus, Edinger-Westphal nucleus, internal capsule, SN, RN, GPi, and Tha.

Superior contrast and high resolution on high-field (7T) MR data have enabled to directly visualize and identify sub-cortical structures within the Basal ganglia and thalamic, particularly, STN and its adjacent structures, although the automatic localization of the STN still remains a challenge. Additionally, volumetric models of sub-cortical structures have been built by exploiting multi-contrast of SWI and $T_2W$ images acquired at 7 T magnet, thereby providing the spatial information—location, dimension, and orientation—of the structures.

FIG. 9 shows 3D structures of manually segmented STN and its adjacent structures—SN, Tha, GPi, and RN—in axial or coronal $T_2W$ 7 T MRI (from one of the subjects in this study used for the disclosure). It should be noted that SN, Tha, GPi, and RN have anatomical proximity with the STN and are more feasible to delineate than other neighboring structures of the STN on the high-field (7T) MR data. For other structures of interest, similar relationships should be exploited. Accordingly, we consider SN, Tha, GPi, and RN as potential predictors of the STN and utilize 3D models (manual segmentations in this case, though automatic or semi-automatic can be used as well) of the STN and the predictors obtained at 7 T MR data as the training set to induce the spatial relationship between them. Given the SN, Tha, GPi, RN or even all of them segmented on the real 7 T MR data (from another subject), we can, following the technique introduced in the previous sections, automatically predict the STN from them on the 7 T MR. Nevertheless, since 7 T MR data might not be widely available for clinical use, the STN prediction on the conventional MR data (1.5 T) needs to be further taken into account.

Figure 11:
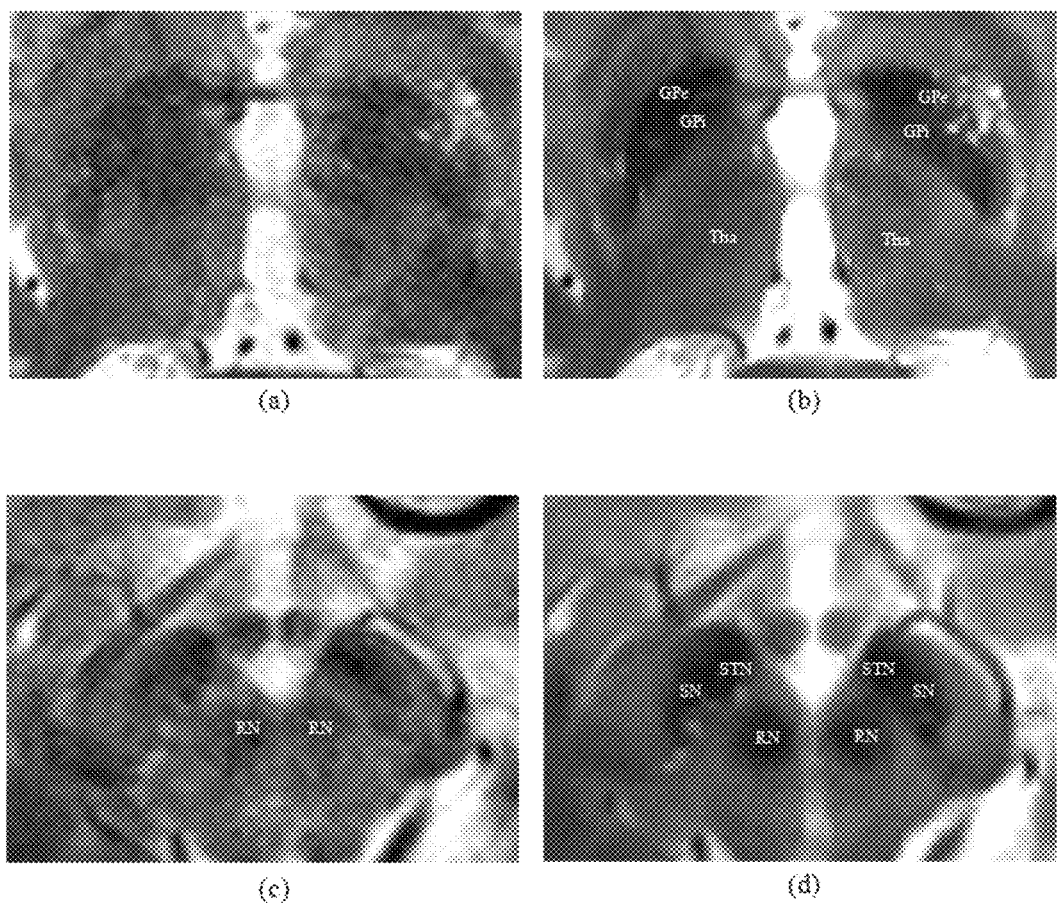
FIG. 11 illustrates the visual comparison of 1.5 T and 7 T on a T2W MR imaging. FIG. (a) and (b) show GPe, GPi, and Tha regions on the 1.5 T and the 7 T MR data, respectively, in axial direction. SN, STN, and RN regions are shown in (c) for 1.5 T, and in (d) for the 7 T MR imaging in the axial plane.

FIG. 11 shows SN, STN, Tha, GP and RN regions in axial $T_2W$ images obtained with 1.5 T and 7 T MR imaging, respectively. Axial $T_2W$ 7 T MR data was registered onto the $T_2W$ 1.5 T MR data for comparison.

We observe that it is difficult to identify the STN from the SN, the GPi in the GP region, and Tha on the 1.5 T (clinical) MR imaging, due to weak intensities and low SNR within those regions, whereas 7 T MR imaging provides clear visualization for those regions. Also, the RN region is more clearly shown on the 7 T MR imaging than on the 1.5 T MR imaging. However, note that the RN is easier to identify than other structures on the 1.5 T MR imaging. Moreover, several studies have utilized the RN (e.g., relative positions of the STN to the RN) as the guidance to implant electrode into the STN during the DBS. On the 1.5 T MR data, we then choose the RN structure as an automatic predictor of the STN, since it is both fairly visible and is in the neighborhood of the STN. The STN on the real 1.5 T MR data is then automatically predicted from the RN obtained on the same data by exploiting their spatial relationship induced on the 7 T MR training data.

In our prediction framework, surface landmark point vectors for each side of the predictors—SN, RN, GPi, or Tha—in the training sets obtained on the 7 T MR imaging are represented as $x_i$ and each side (hemisphere) of pre-segmented predictors on the real data (i.e., SN, RN, GPi, or Tha on the 7 T MR imaging or only RN on the 1.5 T MR imaging) are encoded as their surface landmark vectors $x^{(p)}$, respectively.

Experimental verification. Prediction Measurements. To stress the value of the disclosure and invention, and also some of the particular embodiments here introduced, we now describe as a form of illustration, some of the experimental results we obtained using implementations as those described and exemplified above.

The prediction accuracy is measured by the Dice Coefficient (DC) shape similarity, the average distance between surface landmark points, and the errors in centroid, dimension, and orientation between each predicted STN and its ground truth (i.e., manually segmented STN). The DC value is calculated as the similarity measurement for shapes by $2(V_A \cap V_B)/(V_A+V_B)$, where $V_A$ and $V_B$ are the respective volumes of structures A and B being compared. The mean squared error (MSE) of surface landmark points between manually segmented and predicted STN, $\in_{MSE}$, is measured as $\|y^{(m)} - y^{(p)}\|^2/n_y$, where $y^{(m)}$ and $y^{(p)}$ are 3D representation of surface landmark points for manual segmented and predicted STN, respectively, and $n_y$ is the total number of the points in 3D. Note that $y^{(m)} \in \mathbb{R}^{n_y \times 3}$ and $y^{(p)} \in \mathbb{R}^{n_y \times 3}$, comparing to $y^{(p)} \in \mathbb{R}^{3n_y}$.

Furthermore, we compute the centroids $g=(g_{cor}, g_{sag}, g_{axi})$ in coronal, sagittal, and axial direction, the lengths of three semi-axes (radii) $l=(l_x, l_y, l_z)$, and the orientation angles $o=(\phi, \theta, \psi)$ for inertia ellipsoids of the predicted STNs (i.e., 3D shapes reconstructed from the predicted surface landmark points of the STN) and its manual segmentation, respectively, to analyze the similarity of their geometric information. More specifically, g is calculated as the mean of each coordinates for the landmark points. l is computed from the first three largest eigenvalues obtained by performing PCA for $n_y$ centered landmark points. o is obtained calculating the Euler angles from the rotation matrix which consists of the corresponding eigenvectors. Finally, the errors (as $\mathcal{L}^2$ norm), $\in_g$, $\in_l$, and $\in_o$ between measurements of the manually segmented STN and its predicted one are computed.

Evaluation of Predictors. The prediction for the disclosed method was performed of the STN using each structure—SN, RN, GPi, or Tha—from the 7 T MR and evaluated the prediction performance of such predictors. Training sets for the structures on each dataset are built using the leave-one-out method. For example, training sets for dataset 1 consist of landmark point vectors for each structure from datasets 2, 3, 4, and 5, leaving the ones from dataset 1 out. While 5 sets are used here for illustration, the disclosure and its components apply to any number of training datasets.

For each dataset (e.g., for dataset 1), we extract shape parameters $\tilde{\beta}_i^x=(\tilde{\beta}_{i,left}^x; \tilde{\beta}_{i,right}^x)$ and poses $\tilde{\gamma}_i^x=(\tilde{\gamma}_{i,left}^x; \tilde{\gamma}_{i,right}^x)$ for the left and the right structures of each predictor of the STN (i.e., SN, RN, GPi, or Tha on the 7 T MR data), and shape parameters $\tilde{\beta}_i^y$ and poses $\tilde{\gamma}_i^y$ for each side of the STN, from surface landmark points of their manual segmentations in the training sets (from dataset 2 to 5). The PLSR is then performed on a set of shape parameters $X=\{\tilde{\beta}_2^x, \ldots, \tilde{\beta}_5^x\}^T$ for predictors of the STN and a set of shape parameters $Y=\{\tilde{\beta}_2^y, \ldots, \tilde{\beta}_5^y\}^T$ for the STN in the training sets, yielding regression coefficients for shape parameters $B_{PLS}^\beta$. Similarly, we perform the PLSR on a set of pose parameters $X=\{\tilde{\gamma}_2^x, \ldots, \tilde{\gamma}_5^x\}^T$ for predictors of the STN and a set of pose parameters $Y=\{\tilde{\gamma}_2^y, \ldots, \tilde{\gamma}_5^y\}^T$ for the STN in the training sets, yielding regression coefficients for pose parameters $B_{PLS}^\gamma$, respectively.

The shape parameters $\beta^{y(p)}$ and poses $\gamma^{y(p)}$ are predicted for each side of the STN on the real data (i.e., dataset 1 on the 7 T MR imaging) using the learned relationships $\beta^{y(p)}=$ $$\beta^{x^{(p)T}}$$

$$B_{PLS}\beta \text{ and } \gamma^{y^{(p)}} =$$

$$\gamma^{x^{(p)T}}$$

$B_{PLS}{}^\gamma$, given shape parameters $\beta^{x^{(p)}} = (\beta_{1,left}{}^{x^{(p)}}; \beta_{1,right}{}^{x^{(p)}})$ and poses $\gamma^{x^{(p)}} = (\gamma_{1,left}{}^{x^{(p)}}; \gamma_{1,right}{}^{x^{(p)}})$ for predictors of the STN (i.e., SN, RN, GPi, or Tha on the 7 T MR data) on the real data. Finally, the predicted shape parameters $\beta^{y^{(p)}}$ for each side of the STN in the feature space are reconstructed into surface points $\bar{y}_{est}{}^{(p)}$ in the input space using the pre-image estimation approach and then transformed by the predicted pose parameters $\gamma^{y^{(p)}}$, yielding a complete predicted shape of the STN $\bar{y}^{(p)}$.

The centroids of the STN predicted from the SN, RN, or all of SN, RN, GPi, and Tha are comparable to those of the manually segmented one (i.e., average $\epsilon_g < 1.5$ mm). Dimension errors $\epsilon_l$ of the prediction are similar over all of the predictors with average values less than 1.8 mm. Also, orientation angle errors of the STN predicted from the RN are smaller than using other predictors (i.e., average $\epsilon_o < 8°$), but those are highly variable across the datasets. According to the overall prediction errors, the SN and RN can be considered as quite fair predictors for the STN.

Figure 12:
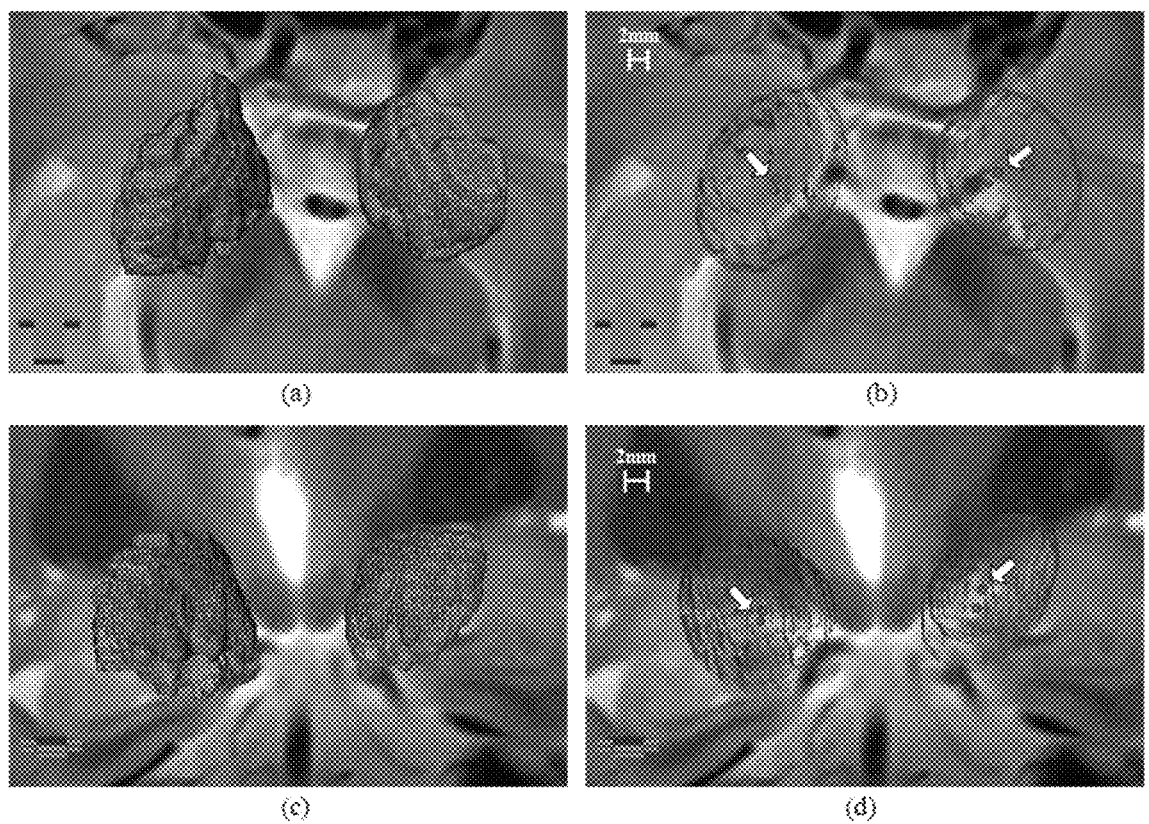
FIG. 12 shows 3D structures and their inertia ellipsoids for STNs predicted using SNs as predictors on the 7T T2W MR training dataset, overlapped with those of manually segmented ones. 3D shapes and corresponding inertia ellipsoids (with centroids) of predicted STNs are shown on the axial plane ((a) and (b)) and on the coronal plane ((c) and (d)), respectively. The blue represents 3D shapes and the inertia ellipsoids (with centroids, see white arrows) of manual segmentations. The red represents 3D shapes and the inertia ellipsoids (with centroids, see white arrows) of predicted STNs. Green arrows are toward the anterior direction. This figure helps to illustrate the performance of one of the embodiments of this disclosure.

In FIG. 12, 3D shapes and their inertia ellipsoids with corresponding centroids of the STNs predicted by using the SN and RN structures, respectively, as predictors on one of the five datasets are shown, overlapping with those of the corresponding manual segmentation. We observe that the centroids, dimensions, and orientations for the predicted STN on the dataset are still comparable to manual segmentations, and the shape is slightly more accurate than in other datasets.

Prediction Results on the 1.5 T MR Dataset. High-field (7T) MR imaging have been successful to visualize the STN, separating its adjacent structure, SN, due to its superior contrast and higher resolution. However, 7 T MR data might not always be available for standard clinical use. Therefore, the STN prediction on the conventional clinical 1.5 T (or 3 T) MR data can provide crucial information for DBS targeting and post-op programming. Prediction of STNs on four (as illustrative example) 1.5 T MR datasets was performed using only visible RN structures on the clinical 1.5 T MRI. For this comparison, we present prediction results obtained using the RN on the corresponding (same subject) 7 T MR datasets and mean of shapes for the STN across training data sets registered onto both 1.5 T and 7 T MR test sets.

Average DC values of the predicted STN on the 1.5 T MR datasets are even better than those on the corresponding 7 T MR dataset. However, it is not still as accurate as manual segmentations. On the other hand, we observe that the centroid distances (average $\epsilon_g$ of left and right sides are less than 2 mm), the dimensions ($\epsilon_l$ is less than 1 mm) on both the 1.5 T and 7 T MR datasets are comparable to those of the manually segmented STN.

Additionally, the measured parameters include distances between centroids of the predicted STNs, mean shape of the STNs, and manually segmented STNs, respectively, and the RN to analyze the relative position of the STN to the RN across the 1.5 T and 7 T MR datasets. Note that we exploited the spatial relationship between the RN and the STN in our prediction framework. Such relative poses between multi-brain structures might provide useful information for diagnosis of neuro-degenerative diseases. Moreover, the RN has been utilized as a reference for DBS targeting of the STN in recent studies.

It was observed that predicted STNs were positioned at 5-8 mm anterior, 3.9-6.7 mm lateral, and 0.7-3.5 mm superior (especially, for manually segmented STNs, 4-7.4 mm anterior, 5.2-7.5 mm lateral, and 0.2-4.2 mm superior) to centroids of the RNs on both sides across the 1.5 T and 7 T MR datasets. Relative positions of predicted STNs, mean shape of the STN, and manually segmented STN to the RN on the 1.5 T MR dataset were similar to those on the 7 T MR dataset. Also, on both 1.5 T and 7 T MR datasets, overall relative positions of predicted STNs to the RN were closer to those of manually segmented STNs to the RN than those of mean shapes of the STN to the RN.

The distance errors of orientation angles $\epsilon_o$ and $\epsilon_{MSE}$ for prediction of the right STN on the 1.5 T MR datasets are 15° and 0.7 mm higher than those on 7 T MR datasets, respectively. Average prediction results for the left side of the STN on both the 1.5 T MR datasets and 7 T MR datasets and mean shapes for the left side of the STN are better than those of the right side. We observed that prediction result of the right STN from one dataset is much worse than those of other datasets. For example, $\epsilon_g$ are 2.98 mm and 2.87 mm, and DC values are 53.5% and 49.4%, comparing to average $\epsilon_g$ (1.89 mm and 1.74 mm) and DC values (60.8% and 57.8%) on the 1.5 T MR and 7 T MR dataset, respectively. This shows that spatial relationship between the right STN and RN on this dataset might be significantly different from the relationship derived from training sets. This disclosure includes the use of multiple datasets thereby enhancing this, the more data the more chances to find the proper brain.

We also measured volumes in the real dimension (mm³) of prediction results, mean shapes, and manual segmentations for the STN. Volumes of manual segmentation on the 1.5 T and 7 T MR datasets should be similar since different volumes between two data sets might lead to inaccurate comparison of DC similarity values. Average volumes of manually segmented STN at 1.5 T are 17 mm³ (left) and 11 mm³ (right) larger than those at 7 T MR datasets (thresholding resampling artifacts after the registration of 7 T MR data onto 1.5 T MR data might result in volume differences between two datasets). Average volumes of predicted STNs and mean shapes are larger than those of manually segmented STNs on both 1.5 T and 7 T MR datasets. Also, we observed that the average volume for the left side of predicted STN on 7 T MR datasets are 14 mm³ larger than that of 1.5 T MR datasets. This explains why the DC value for the left side of the predicted STN on 1.5 T MR datasets in spite of similar measurements, was 7% higher than that on 7 T MR datasets. In other words, volume differences between manual segmentation and prediction of the left STN on the 7 T MR datasets were larger than those on the 1.5 T MR datasets (i.e., 60 mm³ on the 7T and 30 mm³ on the 1.5 T MR dataset). Volumes of predicted STNs for both MR data sets were similar to those of their mean shape for the STN. The larger the dataset, both in size and diversity (e.g., contrasts), the more powerful the prediction is expected.

Overall prediction results from the RN on the 1.5 T MR and 7 T MR datasets are much closer to manually segmented STN than mean shape of the STN across the training datasets, proving the prediction power of our disclosed framework ad invention, fully based on clinical feasible measurements. This clearly illustrates how from clinical MRI, using the disclosed invention, we can localize critical structures for neurosurgery.

Figure 13:
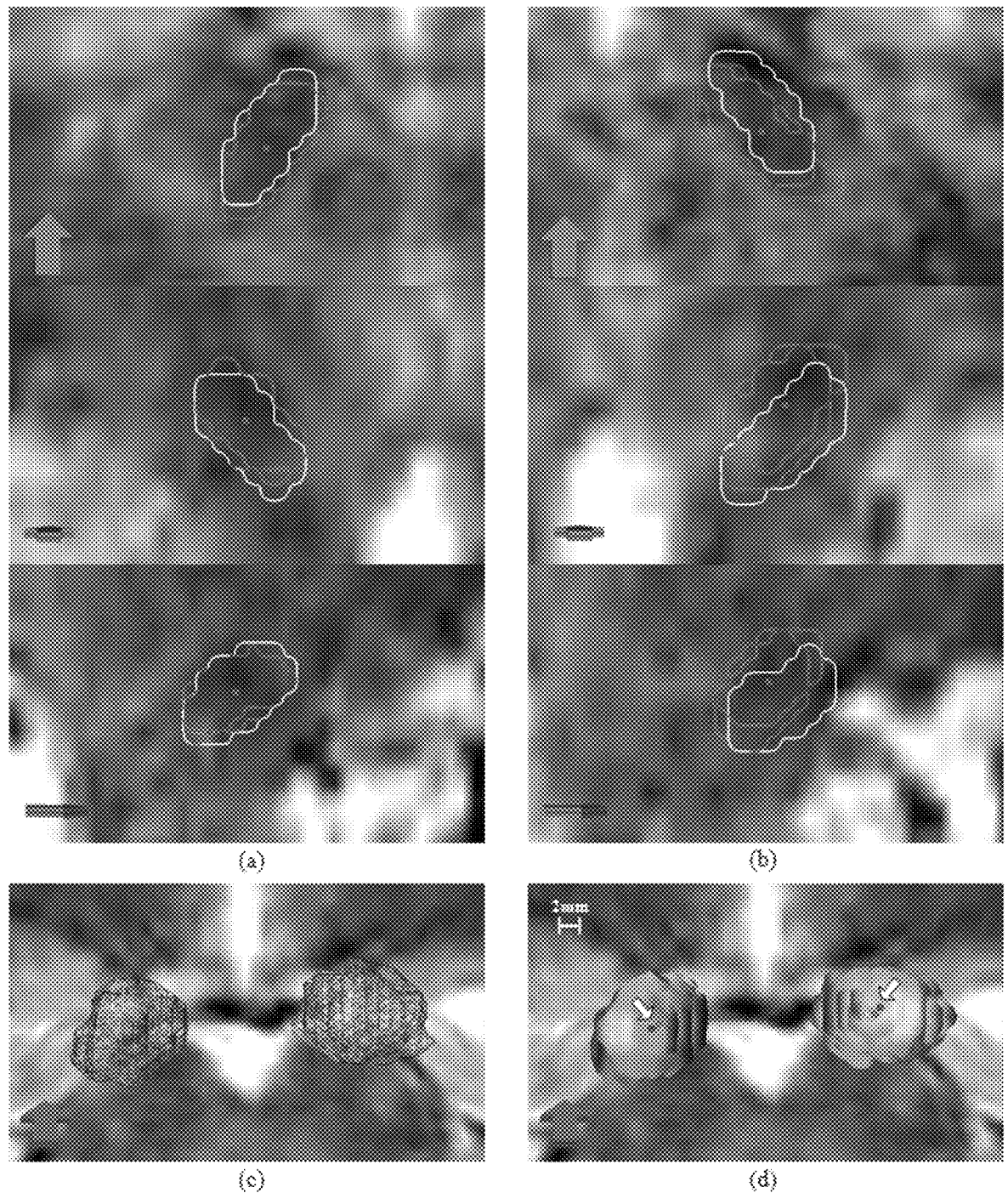
FIG. 13 shows STNs predicted using RNs, mean shapes of the STN across training datasets, and manually segmented STNs on the 1.5 T T2W MRI. 2D contours of predicted STNs, mean of the STNs, and manually segmented STNs (with centroids as the blue points) are shown on the axial plane (top), the coronal plane (middle), and the sagittal plane (bottom), respectively, for the left structure (a) and the right structure (b). 3D surfaces (c) of and inertia ellipsoids (with centroids, see white arrows) (d) of predicted STNs, mean of the STNs, and manually segmented STNs are also shown on the axial plane. The blue, red, and white represent manual segmentations, predicted STNs, and mean of the STNs, respectively. Green arrows are toward the anterior direction. This figure helps to illustrate the performance of one of the embodiments of this disclosure.
Figure 14:
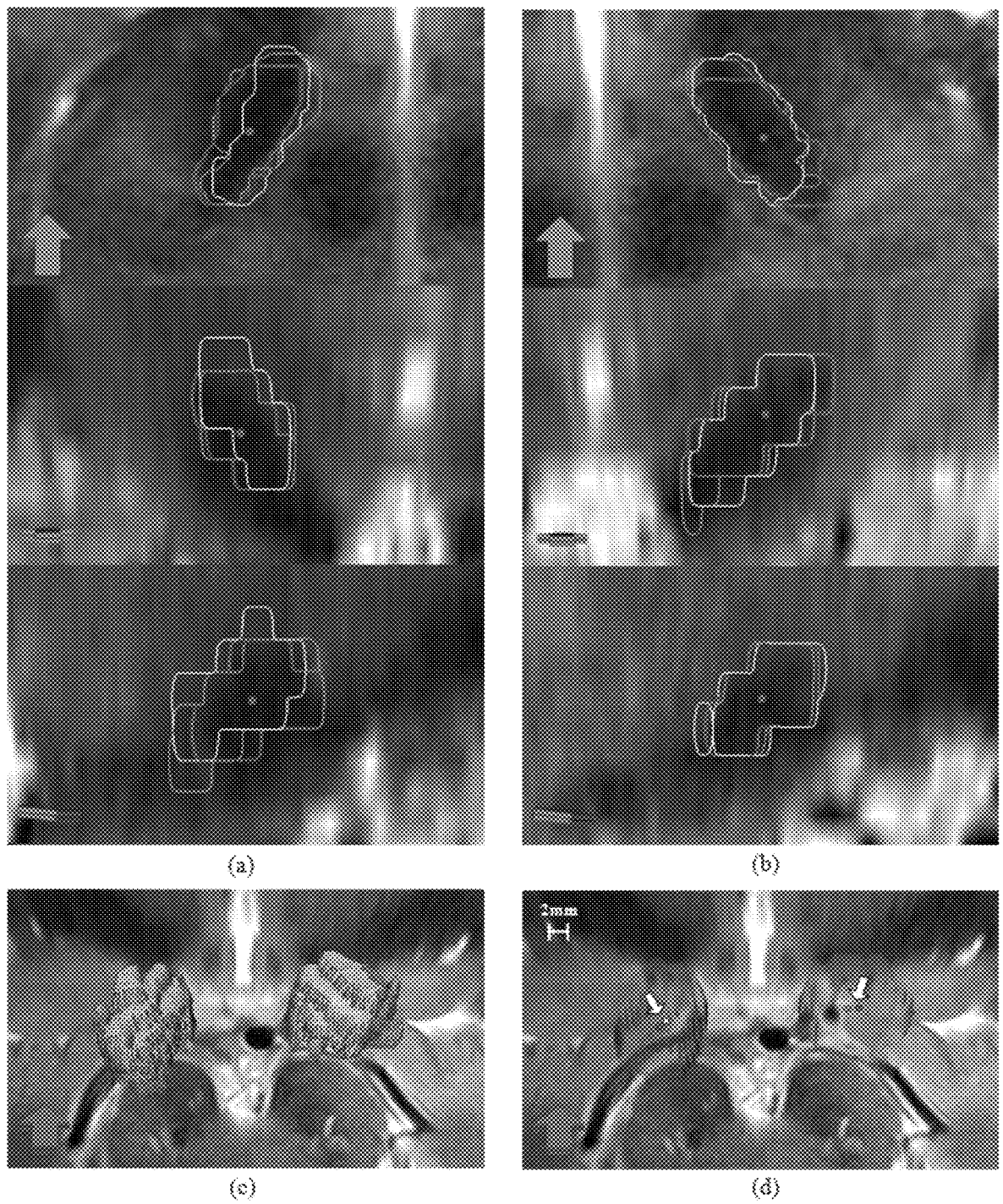
FIG. 14 shows STNs predicted using RNs, mean shapes of the STN across training datasets, and manually segmented STNs on the 7T T2W MRI. This figure helps to illustrate the performance of one of the embodiments of this disclosure.

FIGS. 13 and 14 show contours of the STNs predicted by using the RN structure, manually segmented STNs, and mean of the STN across training datasets in three orthogonal planes, their 3D shapes, and corresponding inertia ellipsoids with centroids on the 1.5 T MR datasets and the 7 T MR datasets, respectively, from a specific subject. Also, we provide centroid positions of predicted STN and mean shape of the STN, comparing to those of manually segmented STN in coronal, sagittal, and axial direction. We then measure relative positions of centroids of the STNs to the RNs.

On this 1.5 T MR data, the STN was more accurately predicted than that on the other datasets and on the corresponding 7 T MR data, showing higher DC values and overall lower distance errors (e.g., $\in_g$<1 mm and $\in_f$<0.5 mm on both sides). We also observed that relative positions of predicted STN to the RN on the 1.5 T MR dataset are closer to those of manually segmented STN to the RN than those of mean shapes of the STN to the RN (especially, on the right side of the STN).

Furthermore, the prediction results on this 1.5 T MR dataset are much better than mean shapes of the STN across training sets registered onto the 1.5 T MR dataset, while the prediction results on the 7 T MR dataset were similar to mean shapes of the STN across training sets registered onto this 7 T MR dataset. In particular, note that the prediction result of the right STN on the 1.5 T MR dataset was closer to the manual segmentation than that on the 7T MR dataset although its mean shape across training sets on the 1.5 T MR dataset was considerably inaccurate, (see FIG. 13). This shows that the prediction of the right STN on this 1.5 T MR data was more effective than that of the STNs on its corresponding 7 T MR dataset.

It should be noted that the disclosed invention enables us to comparably estimate its location, dimension, and orientation, even on data with low contrast (e.g., 1.5 T MR imaging) or occlusions (e.g., noise) within the STN region. This is done exploiting the spatial dependency between the STN and its predictors, learned from the high-field (7T) MR training data. In particular, the centroids, dimensions, and orientation angles of inertia ellipsoids for the predicted STNs may provide very useful information for more precise DBS targeting within the region.

From STN prediction tests on the 7 T MR training datasets the disclosed invention demonstrates that SN and RN structures are better predictors of the STN than GPi and Tha, with higher DC similarity values and lower average errors in centroids, dimensions, and orientations, indicating that those structures provide more significant information about the shape and pose of the STN. Additionally, if all of SN, RN, GPi, and Tha are available on the 7 T MR test data, the multiple structures can be considered as the fair predictor of the STN with their comparable measurements. Although Tha is one of the most adjacent structures to the STN (see FIG. 9(b)), we observed that predicted results obtained using Tha as predictors are slightly worse than using other predictors, particularly, for centroid errors $\in_g$, orientation angle errors $\in_o$, and MSE of surface landmark points $\in_{MSE}$. Note that the Tha structure has relatively larger volume and thus the distance of centroids between the STN and the Tha is much larger than other predictors. Also, manual segmentation of the Tha might not be as precise as that of other predictors. These factors may result in inaccurate poses of the predicted STN. All this should be taken into consideration when applying this invention to these and other brain structures.

Moreover, the method also demonstrate that the RN structure plays a role as a good predictor for the STN on the 1.5 T MR dataset. The overall predicted results of the STN from the RN on the 1.5 T MR imaging were similar to those obtained from the RN on 7 T MR imaging. Although the complete shape of the predicted STN is not as accurate as manually segmented STNs, pose information—centroid and dimension—of the predicted STN was comparable to those of manual segmented STNs.

Average DC values of the predicted STN on the 1.5 T MR imaging are better than those on the 7 T MR imaging although distance errors of orientation angles on the 1.5 T MR dataset are higher, since average volumes of the predicted STN on the 1.5 T MR imaging are closer to the manual segmentation of the STN. Also, accordingly to the disclosed method, the average number of surface landmark points for the STN predicted on the 1.5 T MR imaging are much smaller than that of the STN predicted on the 7 T MR imaging (e.g., average 146 points on the 1.5 T MR dataset and average 436 points on the 7 T MR dataset). This might lead to slightly more accurate shape prediction for the STN on the 1.5 T MR dataset, but yield higher orientation angle errors.

However, it should be noted that the RN structures segmented on the 7T MR dataset were registered onto the 1.5 T MR dataset and then utilized as a predictor for the STN in this example (if a 7 T MRI is not available for clinical use, the RN can be fully segmented on the 1.5 T MRI and registered onto the 1.5 T MR reference data). The RN here used is considered as more reliable predictor for the STN on the 1.5 T MR data since the RN structure can be more clearly identified on the 7 T MR data rather than 1.5 T MR data.

Relative positions of predicted STNs to the RNs on both 1.5 T and 7 T MR datasets were closer to those between manually segmented STNs and the RN than those between mean shapes of the STN and the RN. Note that we learned the spatial relationship between them (especially, that might be useful for diagnosis of neuro-degenerative diseases) in our prediction framework, while relative poses of the RN were not considered in the mean shapes of the STN.

Moreover, prediction of the STN on both 1.5 T and 7 T MR dataset showed more accurate results when mean shapes of the STN across training datasets are closer to the manual segmentation of the STN. Particularly, distance errors of orientation angles are mainly affected by those of mean shapes across the training datasets. These findings imply that prediction of the STN can be further improved by the global alignment of predictors and the STN on the training datasets onto predictors on the test dataset (thereby poses of the mean shape of the STN across the training sets can be close to its manual segmentations), reducing the pose variability between predictors on the training sets and test set, respectively.

The method exploited the spatial dependency between the STN and RN, obtained from the high-field (7T) MR training data sets, to predict the STN from the RN on the 1.5 T MR imaging. 1.5 T (clinical) $T_1W$ image and high-field 7T $T_2W$ MR imaging have different resolutions (e.g., 0.98×0.98×1 mm³ and 0.4×0.4×2 mm³, respectively), meaning missalignment, that might yield inaccurate poses in the prediction. Accordingly, we normalized STN and RN structures on each 7 T MR training data into the common coordinate space of the 1.5 T MR test data using transformation matrices obtained by registering each 7 T MR training dataset onto 7T MR test data and then registering 7 T MR test data onto 1.5 T MR test data. Moreover, 1.5 T MR and 7 T MR reference data are considered as the common coordinate space of 7 T MR training dataset and 1.5 T MR test set as in FIG. 2(b) in case where the 7 T MR test set corresponding to the 1.5 T MR test data is not available.

The method demonstrates that disclosed approach can directly predict shape and pose of the STN, which while sometimes visible, is still difficult to automatically segment, or may not be visible at all due to limited field of view. Furthermore, even on the clinical 1.5 T MR data, where is not possible to identify the STN, we showed that it can be predicted using the RN structure which is fairly visible and adjacent to it.

The prediction of the STN by the disclosed method had been exemplified using five training sets. The results here reported can be further improved using larger datasets of high-field (7T) images. Furthermore, as the database and sample size increase, subgroups of specialized cases (e.g., age, sex or even disease- and/or symptom-specific), may prove to enhance the accuracy of the predictors when adapting prediction models to groups. One embodiment of this disclosure includes the grouping of the data based on such information. Finally, anatomical information related with the variability of STNs such as the third ventricle width and bi-putamen distances across a set of training shapes can be considered as additional predictors and incorporated into the proposed disclosure.

Embodiments of the disclosed systems and methods enable neurosurgeons to engage in far more sophisticated and accurate surgery and DB S implantation procedures. In particular, the ability to avoid blood vessels and vital neural structures, and to select a more accurate initial target and path for DBS implantation, will have the potential to reduce the time required for DBS implantation, as well as the rate of complications. The system and methods disclosed will enhance the ability to engage in automated procedures such as robotic surgery. In such a scenario, the patient specific atlas may dictate to the robotic system the target and the entire penetration path. Tele-surgery will also benefit from the use of higher quality, more flexible imaging techniques. The ability to improve depiction of difficult-to-image tissues such as white matter will enable neurosurgeons to target tissues previously out of reach.

It will be understood that the system and method may be embodied in other specific forms without departing from the spirit or central characteristics thereof. The present examples and embodiments, therefore, are to be considered in all respects as illustrative and not restrictive, and the system method is not to be limited to the details given herein.

What is claimed is:

1. A method for generating an image, comprising:
    accessing a database including a plurality of image files of three-dimensional body portions including structures of interest (SOI) of a plurality of subjects, wherein the database includes one or more first image files of images of a first subject defined by a first contrast, and one or more second image files of images of the first subject defined by a second contrast that is greater than the first contrast;
    selecting a plurality of image files from the database as a training set, including at least one of the first image files and at least one of the second image files;
    processing the training set and generating from the training set information representative of the SOI of the image files of the training set;
    receiving a patient image file of three-dimensional body portions including the patient's structure of interest;
    processing the patient image file based upon the information representative of the SOI of the image files of the training set to generate a patient-specific atlas identifying one or more of a shape, location, size or orientation of the patient's structure of interest in the patient image file.

2. The method of claim 1, wherein the first and second image files are defined by a first coordinate space.

3. The method of claim 2, further comprising:
    receiving a third image file of the three-dimensional body portion of the first subject including the subject's SOI, wherein the third image file is defined by a second coordinate space that is different than the first coordinate space, and the second contrast; and
    generating the second image file from the third image file, comprising:
        segmenting the subject's SOI in the third image file; and
        transforming the segmented SOI into the first coordinate space.

4. The method of claim 1 wherein the patient image file is defined by a contrast that is less than the second contrast.

5. The method of claim 1, wherein generating the information representative of the SOI of the image files comprises generating predictor information.

6. The method of claim 1, further comprising:
    receiving a post-implantation image file of the three dimensional body portions including the patient's structure of interest after insertion of an implant into the patient's structure of interest; and
    merging the post-implantation image with the patient-specific atlas to form a post-implantation composite image.

7. The method of claim 1, wherein the patient image file and the post-implantation image file are defined by a contrast that is less than the second contrast.

8. A method for generating training image files for use in connection with the segmentation of structures of interest in a patient image file, comprising:
    receiving a first image file of a three-dimensional body portion of a training subject including the training subject's structure of interest (SOI), wherein the first image file is defined by a first coordinate space and a first contrast;
    receiving a second image file of the three-dimensional body portion of the training subject including the training subject's SOI, wherein the second image file is defined by a second coordinate space and a second contrast that is greater than the first contrast;
    generating a third image file of the three-dimensional body portion of the training subject including the training subject's SOI, wherein the third image file is defined by the first coordinate space and the second contrast, comprising:
        segmenting the subject's SOI in the second image file; and
        transforming the segmented SOI into the first coordinate space.

9. A method for generating an image, comprising:
    selecting a training set of images, including at least one first image file of a first subject including a structure of interest (SOI) defined by a first coordinate space and a first contrast, and at least one second image file of the first subject including the SOI defined by the first coordinate space and a second contrast that is greater than the first contrast;

processing the selected training set and generating information representative of the SOI of the training set;

receiving a patient image file of three-dimensional body portions including the patient's structure of interest; and processing the patient image file based upon the information representative of the SOI of the training set to generate a patient-specific atlas identifying one or more of a shape, location, size or orientation of the patient's structure of interest in the patient image file.

10. The method of claim 9, further comprising generating the second image file, comprising:

receiving a third image file of the three-dimensional body portion of the first subject including the subject's SOI, wherein the third image file is defined by a second coordinate space that is different than the first coordinate space, and the second contrast; and segmenting the subject's SOI in the third image file; and transforming the segmented SOI in the third image file into the first coordinate space.

11. The method of claim 9, wherein the patient image file is defined by a contrast that is less than the second contrast.

12. The method of claim 9, wherein generating the information representative of the SOI of the image files comprises generating predictor information.

13. The method of claim 9, further comprising:

receiving a post-implantation image file of the three dimensional body portions including the patient's structure of interest after insertion of an implant into the patient's structure of interest; and merging the post-implantation image with the patient-specific atlas to form a post-implantation composite image.

14. The method of claim 8, wherein the patient image file is defined by a contrast that is less than the second contrast.

15. The method of claim 8, wherein generating the information representative of the SOI of the image files comprises generating predictor information.

16. The method of claim 8, further comprising:

receiving a post-implantation image file of the three dimensional body portions including the patient's structure of interest after insertion of an implant into the patient's structure of interest; and merging the post-implantation image with the patient-specific atlas to form a post-implantation composite image.

* * * * *